(12) United States Patent
Yu et al.

(10) Patent No.: US 12,735,694 B2
(45) Date of Patent: Sep. 15, 2026

(54) MUTANT ENZYME, USE THEREOF AND PROCESS FOR PREPARING TRIPEPTIDE BY USING ENZYMATIC METHOD

(71) Applicant: SHENZHEN READLINE BIOTECH CO., LTD., Shenzhen (CN)

(72) Inventors: Tiemei Yu, Shenzhen (CN); Junfeng Pan, Shenzhen (CN); Jian Liu, Shenzhen (CN)

(73) Assignee: SHENZHEN READLINE BIOTECH CO., LTD., Shenzhen (CN)

( * ) Notice: Subject to any disclaimer, the term of this patent is extended or adjusted under 35 U.S.C. 154(b) by 712 days.

(21) Appl. No.: 18/035,736

(22) PCT Filed: Sep. 9, 2021

(86) PCT No.: PCT/CN2021/117378

§ 371 (c)(1),
(2) Date: May 6, 2023

(87) PCT Pub. No.: WO2022/095590

PCT Pub. Date: May 12, 2022

(65) Prior Publication Data

US 2023/0407286 A1 Dec. 21, 2023

(30) Foreign Application Priority Data

Nov. 6, 2020 (CN) ......................... 202011231194.8

(51) Int. Cl.
*C12N 9/00* (2006.01)
*C12P 21/02* (2006.01)

(52) U.S. Cl.
CPC ................ *C12N 9/93* (2013.01); *C12P 21/02* (2013.01); *C12Y 603/02003* (2013.01)

(58) Field of Classification Search
None
See application file for complete search history.

(56) References Cited

U.S. PATENT DOCUMENTS

2008/0213827 A1 9/2008 Hashimoto et al.

FOREIGN PATENT DOCUMENTS

CN 1997738 A 7/2007
CN 104059936 A 9/2014

(Continued)

OTHER PUBLICATIONS

Wang et al., Enzyme and Microbial Technology 136: 109537 (2020).*

(Continued)

*Primary Examiner* — Erin M. Bowers
(74) *Attorney, Agent, or Firm* — Yue (Robert) Xu; Apex Attorneys at Law, LLP

(57) ABSTRACT

The present invention relates to the technical field of biochemistry. Disclosed are a mutant enzyme, the use thereof and a process for preparing a tripeptide by using an enzymatic method. The mutant enzyme comprises: glycine and L-histidine ligase GHS, and tripeptide ligase HKS; or a fusion enzyme of the two. Glycine and L-histidine ligase activity is achieved by means of modifying an Lal enzyme, so as to obtain the GHS enzyme; and the ability for synthesizing dipeptide glycine-L-histidine and L-lysine is achieved by means of using a gshB enzyme, so as to obtain the HKS enzyme. On this basis, the GHS enzyme is further fused with the HKS enzyme by means of using a polypeptide chain, and then a bifunctional enzyme GHKS that links glycine, L-histidine and L-lysine in one step can be constructed, so that a tripeptide is conveniently prepared with a high yield. With regard to the large amount of ATP required in an enzymatic reaction, polyphosphate kinase can be used for cyclic regeneration, such that the amount of ATP is greatly reduced.

7 Claims, 2 Drawing Sheets

Specification includes a Sequence Listing.

(56) References Cited

FOREIGN PATENT DOCUMENTS

| | | | |
|---|---|---|---|
| CN | 104328092 | A | 2/2015 |
| CN | 110777123 | A | 2/2020 |
| CN | 112280755 | A | 1/2021 |
| WO | 2008052428 | A1 | 5/2008 |

OTHER PUBLICATIONS

International Search Report for PCT/CN2021/117378 mailed Nov. 25, 2021, ISA/CN.
Wang Tao et al., L-amino acid ligase: A promising alternative for the biosynthesis of L-dipeptides, Enzyme and Microbial Technology, vol. 136, No. 2020, Feb. 26, 2020.
Zhen Zhou et al., Preparation of short peptide derivative and application in daily chemical product, Detergent & Cosmetics, vol. 34 No. Jan. 1, 2011.
Pitzer. J. et al.,Amides in Nature Biocatalysis, Journal of Biotechnology, vol. 235, No. 2016, Mar. 17, 2016.
Xiang Hong et al., Enzymatic Synthesis ofL-alanyl-L-glutamine by L-amino Acid Ligase from Bacillus Subtilis, Bulletin of Fermentation Science and Technology vol. 46 No. May 2, 2017.
Genpept. “Multispecies: ATP-grasp domain-containing protein [*Pseudomonas syringae* group]” NCBI reference sequence No. WP 005771914.1 Sep. 3, 2018.

* cited by examiner

SEQUENCE LISTING

<160> NUMBER OF SEQ ID NOS: 18

<210> SEQ ID NO 1
<211> LENGTH: 419
<212> TYPE: PRT
<213> ORGANISM: Artificial Sequence
<220> FEATURE:
<223> OTHER INFORMATION: Lal

<400> SEQUENCE: 1

Met Thr Gln Ala Lys Glu Asn Ile Leu Val Val Val Asp Gly Tyr Ser
1               5                   10                  15

Ser Gly Ser Gln Leu Pro Thr Leu Met Ala Glu Ser Gly Trp Lys Cys
            20                  25                  30

Val His Val Ser Ser Ser Ala Asn Pro Pro Glu Tyr Tyr Leu Arg Thr
        35                  40                  45

Tyr His Lys Asp Glu Tyr Ile Ala His Phe Glu Tyr Gln Gly Asp Ile
    50                  55                  60

Gln Ser Leu Ala Ser Ala Val Glu Ala Trp His Pro Ala Ala Val Leu
65                  70                  75                  80

Pro Gly Thr Glu Ser Gly Val Ile Val Ala Asp Leu Leu Ala Ala Ala
                85                  90                  95

Leu Gln Leu Pro Gly Asn Asp Pro Ser Thr Ser Leu Ala Arg Arg Asp
            100                 105                 110

Lys Tyr Thr Met His Glu Ser Leu Lys Ala Val Gly Leu Arg Ser Met
        115                 120                 125

Asp His Phe Leu Ala Val Asp Arg Asp Ala Leu Ser Ala Trp Ala Glu
    130                 135                 140

Arg Gly Ser Trp Pro Val Val Ile Lys Pro Gln Ala Ser Ala Gly Thr
145                 150                 155                 160

Asp Ser Val Thr Phe Cys Ala Asp Gln Gly Glu Leu Leu Glu Ser Phe
                165                 170                 175

Asp Gln Leu Phe Gly Thr Val Asn Gln Leu Gly Glu Arg Asn Asn Ala
            180                 185                 190

Val Leu Ala Gln Arg Leu Leu Val Gly Pro Glu Tyr Phe Ile Asn Gly
        195                 200                 205

Val Ser Gly His Gly Lys His Leu Ile Thr Glu Ile Trp Arg Ala Asp
    210                 215                 220

Lys Leu Pro Ala Pro Asp Gly Gly Trp Ile Tyr Asp Arg Ala Val Leu
225                 230                 235                 240

Phe Asp Pro Thr Ser Pro Glu Met Gln Glu Ile Val Arg Tyr Val His
                245                 250                 255

Gly Val Leu Asp Ala Leu Gly Ile Arg Tyr Gly Ala Asn His Thr Glu
            260                 265                 270

Leu Ile Val Thr Ala Asp Gly Pro Thr Leu Ile Glu Cys Ala Ser Arg
        275                 280                 285

Leu Ser Gly Gly Leu His Arg Pro Ala Ala Asn Tyr Ala Val Gly Ala
    290                 295                 300

Ser Gln Leu Asp Leu Val Gly Lys Leu Val Arg Glu Gly Glu Ser Ala
305                 310                 315                 320

Ile Asp Asp Ile Leu Gln Thr Trp Gln Pro His Arg Tyr Ala Leu Trp
                325                 330                 335

Gln Val Gln Phe Ile Ser Asn Gln Glu Gly Val Val Ala Arg Ser Ser
            340                 345                 350

Tyr Asp Glu Leu Leu Lys Thr Leu Lys Ser Asn Ala Trp Leu Gln Arg

```
        355                 360                 365

Ala Pro Lys Glu Gly Asp Thr Val Val Lys Thr Val Asp Leu Phe Ser
    370                 375                 380

Ser Pro Gly Ile Val Phe Met Ser His Ala Asp Gly Asn Val Leu His
385                 390                 395                 400

Asp Asp Tyr Arg Thr Val Arg Glu Trp Glu Arg Thr Ser Arg Leu Phe
                405                 410                 415

Ser Val Gln


<210> SEQ ID NO 2
<211> LENGTH: 419
<212> TYPE: PRT
<213> ORGANISM: Artificial Sequence
<220> FEATURE:
<223> OTHER INFORMATION: GHS

<400> SEQUENCE: 2

Met Thr Gln Ala Lys Glu Asn Ile Leu Val Val Val Asp Gly Tyr Ser
1               5                   10                  15

Ser Gly Ser Gln Leu Pro Thr Leu Met Ala Glu Ser Gly Trp Lys Cys
            20                  25                  30

Val His Val Ser Ser Ser Ala Asn Pro Pro Glu Tyr Tyr Leu Arg Thr
        35                  40                  45

Tyr His Lys Asp Glu Tyr Ile Ala His Phe Glu Tyr Gln Gly Asp Ile
    50                  55                  60

Gln Ser Leu Ala Ser Ala Val Glu Ala Trp His Pro Ala Ala Val Leu
65                  70                  75                  80

Pro Gly Thr Lys Ser Gly Val Ile Val Ala Asp Leu Leu Ala Ala Ala
                85                  90                  95

Leu Gln Leu Pro Gly Asn Asp Pro Ser Thr Ser Leu Ala Arg Arg Asp
            100                 105                 110

Lys Tyr Thr Met His Glu Ser Leu Lys Ala Val Gly Leu Arg Ser Met
        115                 120                 125

Asp His Phe Leu Ala Val Asp Arg Asp Ala Leu Ser Ala Trp Ala Glu
    130                 135                 140

Arg Gly Ser Trp Pro Val Val Ile Lys Pro Gln Ala Ser His Asp Thr
145                 150                 155                 160

Asp Ser Val Thr Phe Cys Ala Asp Gln Gly Glu Leu Leu Glu Ser Phe
                165                 170                 175

Asp Gln Leu Phe Gly Thr Val Asn Gln Leu Gly Glu Arg Asn Asn Ala
            180                 185                 190

Val Leu Ala Gln Arg Leu Leu Val Gly Pro Glu Tyr Phe Ile Asn Gly
        195                 200                 205

Val Ser Gly His Gly Lys His Leu Ile Thr Glu Ile Trp Arg Ala Asp
    210                 215                 220

Lys Leu Pro Ala Pro Asp Gly Gly Trp Ile Tyr Asp Arg Ala Val Leu
225                 230                 235                 240

Phe Asp Pro Ile Ser Pro Glu Met Gln Glu Ile Val Arg Tyr Val His
                245                 250                 255

Gly Val Leu Asp Ala Leu Gly Ile Arg Tyr Gly Ala Asn His Thr Glu
            260                 265                 270

Leu Ile Val Thr Ala Asp Gly Pro Thr Leu Ile Glu Cys Ala Ser Arg
        275                 280                 285

Leu Leu Gly Trp Leu His Arg Pro Ala Ala Asn Tyr Ala Val Gly Ala
    290                 295                 300
```

```
Ser Gln Leu Asp Leu Val Gly Lys Leu Val Arg Glu Gly Glu Ser Ala
305                 310                 315                 320

Ile Asp Asp Ile Leu Gln Thr Trp Gln Pro His Arg Tyr Ala Leu Trp
                325                 330                 335

Gln Val Gln Phe Ile Ser Asn Gln Glu Gly Val Val Ala Arg Ser Ser
            340                 345                 350

Tyr Asp Glu Leu Leu Lys Thr Leu Lys Ser Asn Ala Trp Leu Gln Arg
        355                 360                 365

Ala Pro Lys Glu Gly Asp Thr Val Val Lys Thr Val Asp Leu Phe Ser
    370                 375                 380

Ser Pro Gly Ile Val Phe Met Ser His Ala Asp Gly Asn Val Leu His
385                 390                 395                 400

Asp Asp Tyr Arg Thr Val Arg Glu Trp Glu Arg Thr Ser Arg Leu Phe
                405                 410                 415

Ser Val Gln


<210> SEQ ID NO 3
<211> LENGTH: 491
<212> TYPE: PRT
<213> ORGANISM: Artificial Sequence
<220> FEATURE:
<223> OTHER INFORMATION: gshB

<400> SEQUENCE: 3

Met Ala His Tyr Pro Pro Ser Lys Asp Gln Leu Asn Glu Leu Ile Gln
1               5                   10                  15

Glu Val Asn Gln Trp Ala Ile Thr Asn Gly Leu Ser Met Tyr Pro Pro
            20                  25                  30

Lys Phe Glu Glu Asn Pro Ser Asn Ala Ser Val Ser Pro Val Thr Ile
        35                  40                  45

Tyr Pro Thr Pro Ile Pro Arg Lys Cys Phe Asp Glu Ala Val Gln Ile
    50                  55                  60

Gln Pro Val Phe Asn Glu Leu Tyr Ala Arg Ile Thr Gln Asp Met Ala
65                  70                  75                  80

Gln Pro Asp Ser Tyr Leu His Lys Thr Thr Glu Ala Leu Ala Leu Ser
                85                  90                  95

Asp Ser Glu Phe Thr Gly Lys Leu Trp Ser Leu Tyr Leu Ala Thr Leu
            100                 105                 110

Lys Ser Ala Gln Tyr Lys Lys Gln Asn Phe Arg Leu Gly Ile Phe Arg
        115                 120                 125

Ser Asp Tyr Leu Ile Asp Lys Lys Lys Gly Thr Glu Gln Ile Lys Gln
    130                 135                 140

Val Glu Phe Asn Thr Val Ser Val Ser Phe Ala Gly Leu Ser Glu Lys
145                 150                 155                 160

Val Asp Arg Leu His Ser Tyr Leu Asn Arg Ala Asn Lys Tyr Asp Pro
                165                 170                 175

Lys Gly Pro Ile Tyr Asn Asp Gln Asn Met Val Ile Ser Asp Ser Gly
            180                 185                 190

Tyr Leu Leu Ser Lys Ala Leu Ala Lys Ala Val Glu Ser Tyr Lys Ser
        195                 200                 205

Gln Gln Ser Ser Ser Thr Thr Ser Asp Pro Ile Val Ala Phe Ile Val
    210                 215                 220

Gln Arg Asn Glu Arg Asn Val Phe Asp Gln Lys Val Leu Glu Leu Asn
225                 230                 235                 240
```

```
Leu Leu Glu Lys Phe Gly Thr Lys Ser Val Arg Leu Thr Phe Asp Asp
                245                 250                 255

Val Asn Asp Lys Leu Phe Ile Asp Asp Lys Thr Gly Lys Leu Phe Ile
            260                 265                 270

Arg Asp Thr Glu Gln Glu Ile Ala Val Val Tyr Tyr Arg Thr Gly Tyr
        275                 280                 285

Thr Thr Thr Asp Tyr Thr Ser Glu Lys Asp Trp Glu Ala Arg Leu Phe
    290                 295                 300

Leu Glu Lys Ser Phe Ala Ile Lys Ala Pro Asp Leu Leu Thr Gln Leu
305                 310                 315                 320

Ser Gly Ser Lys Lys Ile Gln Gln Leu Leu Thr Asp Glu Gly Val Leu
                325                 330                 335

Gly Lys Tyr Ile Ser Asp Ala Glu Lys Lys Ser Ser Leu Leu Lys Thr
            340                 345                 350

Phe Val Lys Ile Tyr Pro Leu Asp Asp Thr Lys Leu Gly Arg Glu Gly
        355                 360                 365

Lys Arg Leu Ala Leu Ser Glu Pro Ser Lys Tyr Val Leu Lys Pro Gln
    370                 375                 380

Arg Glu Gly Gly Gly Asn Asn Val Tyr Lys Glu Asn Ile Pro Asn Phe
385                 390                 395                 400

Leu Lys Gly Ile Glu Glu Arg His Trp Asp Ala Tyr Ile Leu Met Glu
                405                 410                 415

Leu Ile Glu Pro Glu Leu Asn Glu Asn Asn Ile Ile Leu Arg Asp Asn
            420                 425                 430

Lys Ser Tyr Asn Glu Pro Ile Ile Ser Glu Leu Gly Ile Tyr Gly Cys
        435                 440                 445

Val Leu Phe Asn Asp Glu Gln Val Leu Ser Asn Glu Phe Ser Gly Ser
    450                 455                 460

Leu Leu Arg Ser Lys Phe Asn Thr Ser Asn Glu Gly Gly Val Ala Ala
465                 470                 475                 480

Gly Phe Gly Cys Leu Asp Ser Ile Ile Leu Tyr
                485                 490


<210> SEQ ID NO 4
<211> LENGTH: 491
<212> TYPE: PRT
<213> ORGANISM: Artificial Sequence
<220> FEATURE:
<223> OTHER INFORMATION: HKS

<400> SEQUENCE: 4

Met Ala His Tyr Pro Pro Ser Lys Asp Gln Leu Asn Glu Leu Ile Gln
1               5                   10                  15

Glu Val Asn Gln Trp Ala Ile Thr Asn Gly Leu Ser Met Tyr Pro Pro
            20                  25                  30

Lys Phe Glu Glu Asn Pro Ser Asn Ala Ser Val Ser Pro Val Thr Ile
        35                  40                  45

Tyr Pro Thr Pro Ile Pro Arg Lys Cys Phe Asp Glu Ala Val Gln Ile
    50                  55                  60

Gln Pro Val Phe Asn Glu Leu Tyr Ala Arg Ile Thr Gln Asp Met Ala
65                  70                  75                  80

Gln Pro Asp Ser Tyr Leu His Lys Thr Thr Glu Ala Leu Ala Leu Ser
                85                  90                  95

Asp Ser Glu Phe Thr Gly Lys Leu Trp Ser Leu Tyr Leu Ala Thr Leu
            100                 105                 110
```

```
Lys Ser Ala Gln Tyr Lys Lys Gln Asn Phe Arg Leu Gly Ile Phe Arg
        115                 120                 125

Ser Gln Tyr Leu Ile Asp Lys Lys Lys Gly Thr Glu Gln Ile Lys Gln
    130                 135                 140

Val Leu Phe Ser Thr Phe Ser Val Glu Phe Ala Gly Leu Ser Glu Lys
145                 150                 155                 160

Val Asp Arg Leu His Ser Tyr Leu Asn Arg Ala Asn Lys Tyr Asp Pro
                165                 170                 175

Lys Gly Pro Ile Tyr Asn Asp Gln Asn Met Val Ile Ser Asp Ser Gly
            180                 185                 190

Tyr Leu Leu Ser Lys Ala Leu Ala Lys Ala Val Glu Ser Tyr Lys Ser
        195                 200                 205

Gln Gln Ser Ser Ser Thr Thr Ser Asp Pro Ile Val Ala Phe Ile Val
    210                 215                 220

Gln Arg Asn Ile Arg His Val Phe Thr Gln Lys Val Leu Glu Leu Asn
225                 230                 235                 240

Leu Leu Glu Lys Phe Gly Thr Lys Ser Val Arg Leu Thr Phe Asp Asp
                245                 250                 255

Val Asn Asp Lys Leu Phe Ile Asp Asp Lys Thr Gly Lys Leu Phe Ile
            260                 265                 270

Arg Asp Thr Glu Gln Glu Ile Ala Val Val Tyr Tyr Val Thr Gly Tyr
        275                 280                 285

Thr Thr Thr Asp Tyr Thr Ser Glu Lys Asp Trp Glu Ala Arg Leu Phe
    290                 295                 300

Leu Glu Lys Ser Phe Ala Ile Lys Ala Pro Asp Leu Leu Thr Gln Leu
305                 310                 315                 320

Ser Gly Ser Lys Lys Ile Gln Gln Leu Leu Thr Asp Glu Gly Val Leu
                325                 330                 335

Gly Lys Tyr Ile Ser Asp Ala Glu Lys Lys Ser Ser Leu Leu Lys Thr
            340                 345                 350

Phe Val Lys Ile Tyr Pro Leu Asp Asp Thr Lys Leu Gly Arg Glu Gly
        355                 360                 365

Lys Arg Leu Ala Leu Ser Glu Pro Ser Lys Tyr Val Leu Lys Pro Gln
    370                 375                 380

Arg Glu Asn Gly Gly Asn Asn Val Tyr Lys Glu Asn Ile Pro Asn Phe
385                 390                 395                 400

Leu Lys Gly Ile Glu Glu Arg His Trp Asp Ala Tyr Ile Leu Met Glu
                405                 410                 415

Leu Ile Glu Pro Glu Leu Asn Glu Asn Asn Ile Ile Leu Arg Asp Asn
            420                 425                 430

Lys Ser Tyr Asn Glu Pro Ile Ile Ser Glu Leu Gly Asp Tyr Gly Cys
        435                 440                 445

Val Leu Phe Asn Asp Glu Gln Val Leu Ser Asn Glu Phe Ser Gly Ser
    450                 455                 460

Leu Leu Arg Ser Lys Phe Asn Thr Ser Asn Glu Gly Gly Val Ala Ala
465                 470                 475                 480

Gly Phe Gly Cys Leu Asp Ser Ile Ile Leu Tyr
                485                 490
```

<210> SEQ ID NO 5
<211> LENGTH: 930
<212> TYPE: PRT
<213> ORGANISM: Artificial Sequence
<220> FEATURE:
<223> OTHER INFORMATION: GHKS-1

<400> SEQUENCE: 5

```
Met Thr Gln Ala Lys Glu Asn Ile Leu Val Val Val Asp Gly Tyr Ser
1               5                   10                  15

Ser Gly Ser Gln Leu Pro Thr Leu Met Ala Glu Ser Gly Trp Lys Cys
            20                  25                  30

Val His Val Ser Ser Ser Ala Asn Pro Pro Glu Tyr Tyr Leu Arg Thr
        35                  40                  45

Tyr His Lys Asp Glu Tyr Ile Ala His Phe Glu Tyr Gln Gly Asp Ile
    50                  55                  60

Gln Ser Leu Ala Ser Ala Val Glu Ala Trp His Pro Ala Ala Val Leu
65                  70                  75                  80

Pro Gly Thr Lys Ser Gly Val Ile Val Ala Asp Leu Leu Ala Ala Ala
                85                  90                  95

Leu Gln Leu Pro Gly Asn Asp Pro Ser Thr Ser Leu Ala Arg Arg Asp
            100                 105                 110

Lys Tyr Thr Met His Glu Ser Leu Lys Ala Val Gly Leu Arg Ser Met
        115                 120                 125

Asp His Phe Leu Ala Val Asp Arg Asp Ala Leu Ser Ala Trp Ala Glu
    130                 135                 140

Arg Gly Ser Trp Pro Val Val Ile Lys Pro Gln Ala Ser His Asp Thr
145                 150                 155                 160

Asp Ser Val Thr Phe Cys Ala Asp Gln Gly Glu Leu Leu Glu Ser Phe
                165                 170                 175

Asp Gln Leu Phe Gly Thr Val Asn Gln Leu Gly Glu Arg Asn Asn Ala
            180                 185                 190

Val Leu Ala Gln Arg Leu Leu Val Gly Pro Glu Tyr Phe Ile Asn Gly
        195                 200                 205

Val Ser Gly His Gly Lys His Leu Ile Thr Glu Ile Trp Arg Ala Asp
    210                 215                 220

Lys Leu Pro Ala Pro Asp Gly Gly Trp Ile Tyr Asp Arg Ala Val Leu
225                 230                 235                 240

Phe Asp Pro Ile Ser Pro Glu Met Gln Glu Ile Val Arg Tyr Val His
                245                 250                 255

Gly Val Leu Asp Ala Leu Gly Ile Arg Tyr Gly Ala Asn His Thr Glu
            260                 265                 270

Leu Ile Val Thr Ala Asp Gly Pro Thr Leu Ile Glu Cys Ala Ser Arg
        275                 280                 285

Leu Leu Gly Trp Leu His Arg Pro Ala Ala Asn Tyr Ala Val Gly Ala
    290                 295                 300

Ser Gln Leu Asp Leu Val Gly Lys Leu Val Arg Glu Gly Glu Ser Ala
305                 310                 315                 320

Ile Asp Asp Ile Leu Gln Thr Trp Gln Pro His Arg Tyr Ala Leu Trp
                325                 330                 335

Gln Val Gln Phe Ile Ser Asn Gln Glu Gly Val Val Ala Arg Ser Ser
            340                 345                 350

Tyr Asp Glu Leu Leu Lys Thr Leu Lys Ser Asn Ala Trp Leu Gln Arg
        355                 360                 365

Ala Pro Lys Glu Gly Asp Thr Val Val Lys Thr Val Asp Leu Phe Ser
    370                 375                 380

Ser Pro Gly Ile Val Phe Met Ser His Ala Asp Gly Asn Val Leu His
385                 390                 395                 400

Asp Asp Tyr Arg Thr Val Arg Glu Trp Glu Arg Thr Ser Arg Leu Phe
```

```
                405                 410                 415

Ser Val Gln Gly Gly Gly Gly Ser Gly Gly Gly Gly Ser Gly Gly Gly
            420                 425                 430

Gly Ser Gly Gly Gly Gly Ser Met Ala His Tyr Pro Pro Ser Lys Asp
        435                 440                 445

Gln Leu Asn Glu Leu Ile Gln Glu Val Asn Gln Trp Ala Ile Thr Asn
    450                 455                 460

Gly Leu Ser Met Tyr Pro Pro Lys Phe Glu Glu Asn Pro Ser Asn Ala
465                 470                 475                 480

Ser Val Ser Pro Val Thr Ile Tyr Pro Thr Pro Ile Pro Arg Lys Cys
                485                 490                 495

Phe Asp Glu Ala Val Gln Ile Gln Pro Val Phe Asn Glu Leu Tyr Ala
            500                 505                 510

Arg Ile Thr Gln Asp Met Ala Gln Pro Asp Ser Tyr Leu His Lys Thr
        515                 520                 525

Thr Glu Ala Leu Ala Leu Ser Asp Ser Glu Phe Thr Gly Lys Leu Trp
    530                 535                 540

Ser Leu Tyr Leu Ala Thr Leu Lys Ser Ala Gln Tyr Lys Lys Gln Asn
545                 550                 555                 560

Phe Arg Leu Gly Ile Phe Arg Ser Gln Tyr Leu Ile Asp Lys Lys Lys
                565                 570                 575

Gly Thr Glu Gln Ile Lys Gln Val Leu Phe Ser Thr Phe Ser Val Glu
            580                 585                 590

Phe Ala Gly Leu Ser Glu Lys Val Asp Arg Leu His Ser Tyr Leu Asn
        595                 600                 605

Arg Ala Asn Lys Tyr Asp Pro Lys Gly Pro Ile Tyr Asn Asp Gln Asn
    610                 615                 620

Met Val Ile Ser Asp Ser Gly Tyr Leu Leu Ser Lys Ala Leu Ala Lys
625                 630                 635                 640

Ala Val Glu Ser Tyr Lys Ser Gln Gln Ser Ser Ser Thr Thr Ser Asp
                645                 650                 655

Pro Ile Val Ala Phe Ile Val Gln Arg Asn Ile Arg His Val Phe Thr
            660                 665                 670

Gln Lys Val Leu Glu Leu Asn Leu Leu Glu Lys Phe Gly Thr Lys Ser
        675                 680                 685

Val Arg Leu Thr Phe Asp Asp Val Asn Asp Lys Leu Phe Ile Asp Asp
    690                 695                 700

Lys Thr Gly Lys Leu Phe Ile Arg Asp Thr Glu Gln Glu Ile Ala Val
705                 710                 715                 720

Val Tyr Tyr Val Thr Gly Tyr Thr Thr Thr Asp Tyr Thr Ser Glu Lys
                725                 730                 735

Asp Trp Glu Ala Arg Leu Phe Leu Glu Lys Ser Phe Ala Ile Lys Ala
            740                 745                 750

Pro Asp Leu Leu Thr Gln Leu Ser Gly Ser Lys Lys Ile Gln Gln Leu
        755                 760                 765

Leu Thr Asp Glu Gly Val Leu Gly Lys Tyr Ile Ser Asp Ala Glu Lys
    770                 775                 780

Lys Ser Ser Leu Leu Lys Thr Phe Val Lys Ile Tyr Pro Leu Asp Asp
785                 790                 795                 800

Thr Lys Leu Gly Arg Glu Gly Lys Arg Leu Ala Leu Ser Glu Pro Ser
                805                 810                 815

Lys Tyr Val Leu Lys Pro Gln Arg Glu Asn Gly Gly Asn Asn Val Tyr
            820                 825                 830
```

```
Lys Glu Asn Ile Pro Asn Phe Leu Lys Gly Ile Glu Glu Arg His Trp
        835                 840                 845

Asp Ala Tyr Ile Leu Met Glu Leu Ile Glu Pro Glu Leu Asn Glu Asn
    850                 855                 860

Asn Ile Ile Leu Arg Asp Asn Lys Ser Tyr Asn Glu Pro Ile Ile Ser
865                 870                 875                 880

Glu Leu Gly Asp Tyr Gly Cys Val Leu Phe Asn Asp Glu Gln Val Leu
                885                 890                 895

Ser Asn Glu Phe Ser Gly Ser Leu Leu Arg Ser Lys Phe Asn Thr Ser
            900                 905                 910

Asn Glu Gly Gly Val Ala Ala Gly Phe Gly Cys Leu Asp Ser Ile Ile
        915                 920                 925

Leu Tyr
    930


<210> SEQ ID NO 6
<211> LENGTH: 930
<212> TYPE: PRT
<213> ORGANISM: Artificial Sequence
<220> FEATURE:
<223> OTHER INFORMATION: GHKS-2

<400> SEQUENCE: 6

Met Thr Gln Ala Lys Glu Asn Ile Leu Val Val Val Asp Gly Tyr Ser
1               5                   10                  15

Ser Gly Ser Gln Leu Pro Thr Leu Met Ala Glu Ser Gly Trp Lys Cys
            20                  25                  30

Val His Val Ser Ser Ser Ala Asn Pro Pro Glu Tyr Tyr Leu Arg Thr
        35                  40                  45

Tyr His Lys Asp Glu Tyr Ile Ala His Phe Glu Tyr Gln Gly Asp Ile
    50                  55                  60

Gln Ser Leu Ala Ser Ala Val Glu Ala Trp His Pro Ala Ala Val Leu
65                  70                  75                  80

Pro Gly Thr Lys Ser Gly Val Ile Val Ala Asp Leu Leu Ala Ala Ala
                85                  90                  95

Leu Gln Leu Pro Gly Asn Asp Pro Ser Thr Ser Leu Ala Arg Arg Asp
            100                 105                 110

Lys Tyr Thr Met His Glu Ser Leu Lys Ala Val Gly Leu Arg Ser Met
        115                 120                 125

Asp His Phe Leu Ala Val Asp Arg Asp Ala Leu Ser Ala Trp Ala Glu
    130                 135                 140

Arg Gly Ser Trp Pro Val Val Ile Lys Pro Gln Ala Ser His Asp Thr
145                 150                 155                 160

Asp Ser Val Thr Phe Cys Ala Asp Gln Gly Glu Leu Leu Glu Ser Phe
                165                 170                 175

Asp Gln Leu Phe Gly Thr Val Asn Gln Leu Gly Glu Arg Asn Asn Ala
            180                 185                 190

Val Leu Ala Gln Arg Leu Leu Val Gly Pro Glu Tyr Phe Ile Asn Gly
        195                 200                 205

Val Ser Gly His Gly Lys His Leu Ile Thr Glu Ile Trp Arg Ala Asp
    210                 215                 220

Lys Leu Pro Ala Pro Asp Gly Gly Trp Ile Tyr Asp Arg Ala Val Leu
225                 230                 235                 240

Phe Asp Pro Ile Ser Pro Glu Met Gln Glu Ile Val Arg Tyr Val His
                245                 250                 255
```

```
Gly Val Leu Asp Ala Leu Gly Ile Arg Tyr Gly Ala Asn His Thr Glu
                260                 265                 270

Leu Ile Val Thr Ala Asp Gly Pro Thr Leu Ile Glu Cys Ala Ser Arg
            275                 280                 285

Leu Leu Gly Trp Leu His Arg Pro Ala Ala Asn Tyr Ala Val Gly Ala
    290                 295                 300

Ser Gln Leu Asp Leu Val Gly Lys Leu Val Arg Glu Gly Glu Ser Ala
305                 310                 315                 320

Ile Asp Asp Ile Leu Gln Thr Trp Gln Pro His Arg Tyr Ala Leu Trp
                325                 330                 335

Gln Val Gln Phe Ile Ser Asn Gln Glu Gly Val Val Ala Arg Ser Ser
                340                 345                 350

Tyr Asp Glu Leu Leu Lys Thr Leu Lys Ser Asn Ala Trp Leu Gln Arg
            355                 360                 365

Ala Pro Lys Glu Gly Asp Thr Val Val Lys Thr Val Asp Leu Phe Ser
    370                 375                 380

Ser Pro Gly Ile Val Phe Met Ser His Ala Asp Gly Asn Val Leu His
385                 390                 395                 400

Asp Asp Tyr Arg Thr Val Arg Glu Trp Glu Arg Thr Ser Arg Leu Phe
                405                 410                 415

Ser Val Gln Gly Gly Gly Gly Ser Glu Ala Ala Ala Lys Glu Ala Ala
                420                 425                 430

Ala Lys Gly Gly Gly Gly Ser Met Ala His Tyr Pro Pro Ser Lys Asp
            435                 440                 445

Gln Leu Asn Glu Leu Ile Gln Glu Val Asn Gln Trp Ala Ile Thr Asn
    450                 455                 460

Gly Leu Ser Met Tyr Pro Pro Lys Phe Glu Glu Asn Pro Ser Asn Ala
465                 470                 475                 480

Ser Val Ser Pro Val Thr Ile Tyr Pro Thr Pro Ile Pro Arg Lys Cys
                485                 490                 495

Phe Asp Glu Ala Val Gln Ile Gln Pro Val Phe Asn Glu Leu Tyr Ala
                500                 505                 510

Arg Ile Thr Gln Asp Met Ala Gln Pro Asp Ser Tyr Leu His Lys Thr
            515                 520                 525

Thr Glu Ala Leu Ala Leu Ser Asp Ser Glu Phe Thr Gly Lys Leu Trp
    530                 535                 540

Ser Leu Tyr Leu Ala Thr Leu Lys Ser Ala Gln Tyr Lys Lys Gln Asn
545                 550                 555                 560

Phe Arg Leu Gly Ile Phe Arg Ser Gln Tyr Leu Ile Asp Lys Lys Lys
                565                 570                 575

Gly Thr Glu Gln Ile Lys Gln Val Leu Phe Ser Thr Phe Ser Val Glu
                580                 585                 590

Phe Ala Gly Leu Ser Glu Lys Val Asp Arg Leu His Ser Tyr Leu Asn
            595                 600                 605

Arg Ala Asn Lys Tyr Asp Pro Lys Gly Pro Ile Tyr Asn Asp Gln Asn
    610                 615                 620

Met Val Ile Ser Asp Ser Gly Tyr Leu Leu Ser Lys Ala Leu Ala Lys
625                 630                 635                 640

Ala Val Glu Ser Tyr Lys Ser Gln Gln Ser Ser Ser Thr Thr Ser Asp
                645                 650                 655

Pro Ile Val Ala Phe Ile Val Gln Arg Asn Ile Arg His Val Phe Thr
                660                 665                 670
```

```
Gln Lys Val Leu Glu Leu Asn Leu Leu Glu Lys Phe Gly Thr Lys Ser
        675                 680                 685

Val Arg Leu Thr Phe Asp Asp Val Asn Asp Lys Leu Phe Ile Asp Asp
    690                 695                 700

Lys Thr Gly Lys Leu Phe Ile Arg Asp Thr Glu Gln Glu Ile Ala Val
705                 710                 715                 720

Val Tyr Tyr Val Thr Gly Tyr Thr Thr Thr Asp Tyr Thr Ser Glu Lys
                725                 730                 735

Asp Trp Glu Ala Arg Leu Phe Leu Glu Lys Ser Phe Ala Ile Lys Ala
            740                 745                 750

Pro Asp Leu Leu Thr Gln Leu Ser Gly Ser Lys Lys Ile Gln Gln Leu
        755                 760                 765

Leu Thr Asp Glu Gly Val Leu Gly Lys Tyr Ile Ser Asp Ala Glu Lys
    770                 775                 780

Lys Ser Ser Leu Leu Lys Thr Phe Val Lys Ile Tyr Pro Leu Asp Asp
785                 790                 795                 800

Thr Lys Leu Gly Arg Glu Gly Lys Arg Leu Ala Leu Ser Glu Pro Ser
                805                 810                 815

Lys Tyr Val Leu Lys Pro Gln Arg Glu Asn Gly Gly Asn Asn Val Tyr
            820                 825                 830

Lys Glu Asn Ile Pro Asn Phe Leu Lys Gly Ile Glu Glu Arg His Trp
        835                 840                 845

Asp Ala Tyr Ile Leu Met Glu Leu Ile Glu Pro Glu Leu Asn Glu Asn
    850                 855                 860

Asn Ile Ile Leu Arg Asp Asn Lys Ser Tyr Asn Glu Pro Ile Ile Ser
865                 870                 875                 880

Glu Leu Gly Asp Tyr Gly Cys Val Leu Phe Asn Asp Glu Gln Val Leu
                885                 890                 895

Ser Asn Glu Phe Ser Gly Ser Leu Leu Arg Ser Lys Phe Asn Thr Ser
            900                 905                 910

Asn Glu Gly Gly Val Ala Ala Gly Phe Gly Cys Leu Asp Ser Ile Ile
        915                 920                 925

Leu Tyr
    930
```

<210> SEQ ID NO 7
<211> LENGTH: 286
<212> TYPE: PRT
<213> ORGANISM: Artificial Sequence
<220> FEATURE:
<223> OTHER INFORMATION: PPK

<400> SEQUENCE: 7

```
Met Pro Met Val Ala Ala Val Glu Phe Ala Lys Ser Pro Ala Glu Val
1               5                   10                  15

Leu Arg Val Gly Ser Gly Phe Ser Leu Ala Gly Val Asp Pro Glu Ser
            20                  25                  30

Thr Pro Gly Tyr Thr Gly Val Lys Ala Asp Gly Lys Ala Leu Leu Ala
        35                  40                  45

Ala Gln Asp Ala Arg Leu Ala Glu Leu Gln Glu Lys Leu Phe Ala Glu
    50                  55                  60

Gly Lys Phe Gly Asn Pro Lys Arg Leu Leu Leu Ile Leu Gln Ala Met
65                  70                  75                  80

Asp Thr Ala Gly Lys Gly Gly Ile Val Ser His Val Val Gly Ala Met
                85                  90                  95
```

```
Asp Pro Gln Gly Val Gln Leu Thr Ala Phe Lys Ala Pro Thr Asp Glu
            100                 105                 110

Glu Lys Ser His Asp Phe Leu Trp Arg Ile Glu Lys Gln Val Pro Ala
        115                 120                 125

Ala Gly Met Val Gly Val Phe Asp Arg Ser Gln Tyr Glu Asp Val Leu
    130                 135                 140

Ile His Arg Val His Gly Trp Ala Asp Ala Ala Glu Leu Glu Arg Arg
145                 150                 155                 160

Tyr Ala Ala Ile Asn Asp Phe Glu Ser Arg Leu Thr Glu Gln Gly Thr
                165                 170                 175

Thr Ile Val Lys Val Met Leu Asn Ile Ser Lys Asp Glu Gln Lys Lys
            180                 185                 190

Arg Leu Ile Ala Arg Leu Asp Asp Pro Ser Lys His Trp Lys Tyr Ser
        195                 200                 205

Arg Gly Asp Leu Ala Glu Arg Ala Tyr Trp Asp Asp Tyr Met Asp Ala
    210                 215                 220

Tyr Ser Val Ala Phe Glu Lys Thr Ser Thr Glu Ile Ala Pro Trp His
225                 230                 235                 240

Val Val Pro Ala Asn Lys Lys Trp Tyr Ala Arg Ile Ala Val Gln Gln
                245                 250                 255

Leu Leu Leu Asp Ala Leu Gly Gly Leu Gln Leu Asp Trp Pro Lys Ala
            260                 265                 270

Asp Phe Asp Val Ala Ala Glu Arg Ala Leu Val Val Glu Ser
        275                 280                 285


<210> SEQ ID NO 8
<211> LENGTH: 214
<212> TYPE: PRT
<213> ORGANISM: Artificial Sequence
<220> FEATURE:
<223> OTHER INFORMATION: ADK

<400> SEQUENCE: 8

Met Arg Ile Ile Leu Leu Gly Ala Pro Gly Ala Gly Lys Gly Thr Gln
1               5                   10                  15

Ala Gln Phe Ile Met Glu Lys Tyr Gly Ile Pro Gln Ile Ser Thr Gly
            20                  25                  30

Asp Met Leu Arg Ala Ala Val Lys Ser Gly Ser Glu Leu Gly Lys Gln
        35                  40                  45

Ala Lys Asp Ile Met Asp Ala Gly Lys Leu Val Thr Asp Glu Leu Val
    50                  55                  60

Ile Ala Leu Val Lys Glu Arg Ile Ala Gln Glu Asp Cys Arg Asn Gly
65                  70                  75                  80

Phe Leu Leu Asp Gly Phe Pro Arg Thr Ile Pro Gln Ala Asp Ala Met
                85                  90                  95

Lys Glu Ala Gly Ile Asn Val Asp Tyr Val Leu Glu Phe Asp Val Pro
            100                 105                 110

Asp Glu Leu Ile Val Asp Arg Ile Val Gly Arg Arg Val His Ala Pro
        115                 120                 125

Ser Gly Arg Val Tyr His Val Lys Phe Asn Pro Pro Lys Val Glu Gly
    130                 135                 140

Lys Asp Asp Val Thr Gly Glu Glu Leu Thr Thr Arg Lys Asp Asp Gln
145                 150                 155                 160

Glu Glu Thr Val Arg Lys Arg Leu Val Glu Tyr His Gln Met Thr Ala
                165                 170                 175
```

```
Pro Leu Ile Gly Tyr Tyr Ser Lys Glu Ala Glu Ala Gly Asn Thr Lys
            180                 185                 190

Tyr Ala Lys Val Asp Gly Thr Lys Pro Val Ala Glu Val Arg Ala Asp
        195                 200                 205

Leu Glu Lys Ile Leu Gly
    210


<210> SEQ ID NO 9
<211> LENGTH: 1260
<212> TYPE: DNA
<213> ORGANISM: Artificial Sequence
<220> FEATURE:
<223> OTHER INFORMATION: Lal

<400> SEQUENCE: 9

atgacgcagg ccaaggaaaa catcttagtt gtggtcgatg gctactcctc aggcagtcag     60

ttgcctaccc tgatggcgga atccggctgg aagtgtgttc atgtctcgtc ctcggctaac    120

cccccggagt attacctgcg tacataccat aaggatgagt acatagctca ctttgagtat    180

caaggtgata tacagtcact tgctagtgct gttgaggcgt ggcatcccgc cgcagttctt    240

cctggtacgg aaagtggagt tattgtcgct gatttactgg cggctgcttt gcaattgcca    300

ggcaatgacc cgtcgacctc cctggcgaga cgcgacaaat atacgatgca tgagtcattg    360

aaagcggtgg gacttcggag tatggaccat ttccttgccg tcgatcgtga tgctttatca    420

gcttgggccg agcggggatc ttggccagtg gtaattaaac cccaggcttc ggcaggcaca    480

gacagtgtta cattctgcgc cgatcaggga gaattattag agtcgtttga tcaattgttc    540

ggcactgtga accaattggg tgaacgcaat aatgcagtgc tggctcagcg tctgttggtt    600

ggtcccgagt actttatcaa cggagtttct ggacatggca aacacctgat tacagagatt    660

tggcgtgcag acaagctgcc cgcaccggac gggggttgga tatacgaccg ggccgtgctg    720

tttgacccga cgagtcccga gatgcaggag attgtccgct acgtgcatgg agtattagat    780

gcccttggca tccgctatgg tgcgaaccat acagagctga tcgtaacggc tgatggccca    840

acactgatag aatgtgcctc ccgtttatcc gggggactgc atagacctgc agcgaactat    900

gcggttggcg catcacaact tgacttggtc ggtaaacttg tacgggaagg ggaaagcgct    960

atagatgata tactgcaaac ttggcaacct caccgctacg cattgtggca agtccaattc   1020

atatcgaatc aagagggagt agtggctcgg agttcgtacg acgaacttct taaaacgttg   1080

aaatccaatg cctggttgca acgggctccg aaggaaggcg ataccgtagt caagacagtc   1140

gacctgttca gctcgcccgg aatagtcttt atgtcacacg cagacggtaa tgttctgcac   1200

gacgattatc ggacggtccg ggaatgggag cgtacctcgc gcctgttctc ggtgcagtaa   1260


<210> SEQ ID NO 10
<211> LENGTH: 1260
<212> TYPE: DNA
<213> ORGANISM: Artificial Sequence
<220> FEATURE:
<223> OTHER INFORMATION: GHS

<400> SEQUENCE: 10

atgacgcagg ccaaggaaaa catcttagtt gtggtcgatg gctactcctc aggcagtcag     60

ttgcctaccc tgatggcgga atccggctgg aagtgtgttc atgtctcgtc ctcggctaac    120

cccccggagt attacctgcg tacataccat aaggatgagt acatagctca ctttgagtat    180

caaggtgata tacagtcact tgctagtgct gttgaggcgt ggcatcccgc cgcagttctt    240
```

-continued

```
cctggtacga aaagtggagt tattgtcgct gatttactgg cggctgcttt gcaattgcca    300

ggcaatgacc cgtcgacctc cctggcgaga cgcgacaaat atacgatgca tgagtcattg    360

aaagcggtgg gacttcggag tatggaccat ttccttgccg tcgatcgtga tgctttatca    420

gcttgggccg agcggggatc ttggccagtg gtaattaaac cccaggcttc gcacgacaca    480

gacagtgtta cattctgcgc cgatcaggga gaattattag agtcgtttga tcaattgttc    540

ggcactgtga accaattggg tgaacgcaat aatgcagtgc tggctcagcg tctgttggtt    600

ggtcccgagt actttatcaa cggagtttct ggacatggca aacacctgat tacagagatt    660

tggcgtgcag acaagctgcc cgcaccggac gggggttgga tatacgaccg ggccgtgctg    720

tttgacccga tcagtcccga gatgcaggag attgtccgct acgtgcatgg agtattagat    780

gcccttggca tccgctatgg tgcgaaccat acagagctga tcgtaacggc tgatggccca    840

acactgatag aatgtgcctc ccgtttactc gggtggctgc atagacctgc agcgaactat    900

gcggttggcg catcacaact tgacttggtc ggtaaacttg tacgggaagg ggaaagcgct    960

atagatgata tactgcaaac ttggcaacct caccgctacg cattgtggca agtccaattc   1020

atatcgaatc aagagggagt agtggctcgg agttcgtacg acgaacttct taaaacgttg   1080

aaatccaatg cctggttgca acgggctccg aaggaaggcg ataccgtagt caagacagtc   1140

gacctgttca gctcgcccgg aatagtcttt atgtcacacg cagacggtaa tgttctgcac   1200

gacgattatc ggacggtccg ggaatgggag cgtacctcgc gcctgttctc ggtgcagtaa   1260
```

```
<210> SEQ ID NO 11
<211> LENGTH: 1476
<212> TYPE: DNA
<213> ORGANISM: Artificial Sequence
<220> FEATURE:
<223> OTHER INFORMATION: gshB

<400> SEQUENCE: 11

atggcacact atccaccttc caaggatcaa ttgaatgaat tgatccagga agttaaccaa     60

tgggctatca ctaatggatt atccatgtat cctcctaaat tcgaggagaa cccatcaaat    120

gcatcggtgt caccagtaac tatctatcca accccaattc ctaggaaatg ttttgatgag    180

gccgttcaaa tacaaccggt attcaatgaa ttatacgccc gtattaccca agatatggcc    240

caacctgatt cttatttaca taaaacaact gaagcgttag ctctatcaga ttccgagttt    300

actggaaaac tgtggtctct ataccttgct accttaaaat ctgcacagta caaaaagcag    360

aattttaggc taggtatatt tagatcagat tatttgattg ataagaaaaa gggtactgaa    420

cagattaagc aagtcgagtt taatacagtg tcagtgtcat ttgcaggcct tagcgagaaa    480

gttgatagat tgcactctta tttaaatagg gcaaacaagt acgatcctaa aggaccaatt    540

tataatgatc aaaatatggt catttctgat tcaggatacc ttttgtctaa ggcattggcc    600

aaagctgtgg aatcgtataa gtcacaacaa agttcttcta caactagtga tcctattgtc    660

gcattcattg tgcaaagaaa cgagagaaat gtgtttgatc aaaaggtctt ggaattgaat    720

ctgttggaaa aattcggtac caaatctgtt aggttgacgt ttgatgatgt taacgataaa    780

ttgttcattg atgataaaac gggaaagctt ttcattaggg acacagagca ggaaatagcg    840

gtggtttatt acagaacggg ttacacaacc actgattaca cgtccgaaaa ggactgggag    900

gcaagactat tcctcgaaaa aagtttcgca ataaaggccc cagatttact cactcaatta    960

tctggctcca agaaaattca gcaattgttg acagatgagg gcgtattagg taaatacatc   1020

tccgatgctg agaaaaagag tagtttgtta aaaacttttg tcaaaatata tcccttggat   1080
```

```
gatacgaagc ttggcaggga aggcaagagg ctggcattaa gtgagccctc taaatacgtg   1140

ttaaaaccac agcgggaagg tggcggaaac aatgtttata aagaaaatat tcctaatttt   1200

ttgaaaggta tcgaagaacg tcactgggat gcatatattc tcatggagtt gattgaacca   1260

gagttgaatg aaaataatat tatattacgt gataacaaat cttacaacga accaatcatc   1320

agtgaactag gaatttatgg ttgcgttcta tttaacgacg agcaagtttt atcgaacgaa   1380

tttagtggct cattactaag atccaaattt aatacttcaa atgaaggtgg agtggcggca   1440

ggattcggat gtttggacag tattattctt tactag                             1476
```

```
<210> SEQ ID NO 12
<211> LENGTH: 1476
<212> TYPE: DNA
<213> ORGANISM: Artificial Sequence
<220> FEATURE:
<223> OTHER INFORMATION: HKS

<400> SEQUENCE: 12

atggcacact atccaccttc caaggatcaa ttgaatgaat tgatccagga agttaaccaa     60

tgggctatca ctaatggatt atccatgtat cctcctaaat tcgaggagaa cccatcaaat    120

gcatcggtgt caccagtaac tatctatcca accccaattc ctaggaaatg ttttgatgag    180

gccgttcaaa tacaaccggt attcaatgaa ttatacgccc gtattaccca agatatggcc    240

caacctgatt cttatttaca taaaacaact gaagcgttag ctctatcaga ttccgagttt    300

actggaaaac tgtggtctct ataccttgct accttaaaat ctgcacagta caaaaagcag    360

aattttaggc taggtatatt tagatcacag tatttgattg ataagaaaaa gggtactgaa    420

cagattaagc aagtcctgtt tagtacattc tcagtggaat ttgcaggcct tagcgagaaa    480

gttgatagat tgcactctta tttaaatagg gcaaacaagt acgatcctaa aggaccaatt    540

tataatgatc aaaatatggt catttctgat tcaggatacc ttttgtctaa ggcattggcc    600

aaagctgtgg aatcgtataa gtcacaacaa agttcttcta caactagtga tcctattgtc    660

gcattcattg tgcaaagaaa catcagacat gtgtttactc aaaaggtctt ggaattgaat    720

ctgttggaaa aattcggtac caaatctgtt aggttgacgt ttgatgatgt taacgataaa    780

ttgttcattg atgataaaac gggaaagctt ttcattaggg acacagagca ggaaatagcg    840

gtggtttatt acgtaacggg ttacacaacc actgattaca cgtccgaaaa ggactgggag    900

gcaagactat tcctcgaaaa aagtttcgca ataaaggccc cagatttact cactcaatta    960

tctggctcca agaaaattca gcaattgttg acagatgagg gcgtattagg taaatacatc   1020

tccgatgctg agaaaaagag tagtttgtta aaaacttttg tcaaaatata tcccttggat   1080

gatacgaagc ttggcaggga aggcaagagg ctggcattaa gtgagccctc taaatacgtg   1140

ttaaaaccac agcgggaaaa tggcggaaac aatgtttata aagaaaatat tcctaatttt   1200

ttgaaaggta tcgaagaacg tcactgggat gcatatattc tcatggagtt gattgaacca   1260

gagttgaatg aaaataatat tatattacgt gataacaaat cttacaacga accaatcatc   1320

agtgaactag gagattatgg ttgcgttcta tttaacgacg agcaagtttt atcgaacgaa   1380

tttagtggct cattactaag atccaaattt aatacttcaa atgaaggtgg agtggcggca   1440

ggattcggat gtttggacag tattattctt tactag                             1476

<210> SEQ ID NO 13
<211> LENGTH: 2793
<212> TYPE: DNA
```

<213> ORGANISM: Artificial Sequence
<220> FEATURE:
<223> OTHER INFORMATION: GHKS-1

<400> SEQUENCE: 13

```
atgacgcagg ccaaggaaaa catcttagtt gtggtcgatg gctactcctc aggcagtcag     60
ttgcctaccc tgatggcgga atccggctgg aagtgtgttc atgtctcgtc ctcggctaac    120
cccccggagt attacctgcg tacataccat aaggatgagt acatagctca ctttgagtat    180
caaggtgata tacagtcact tgctagtgct gttgaggcgt ggcatcccgc cgcagttctt    240
cctggtacga aaagtggagt tattgtcgct gatttactgg cggctgcttt gcaattgcca    300
ggcaatgacc cgtcgacctc cctggcgaga cgcgacaaat atacgatgca tgagtcattg    360
aaagcggtgg gacttcggag tatggaccat ttccttgccg tcgatcgtga tgctttatca    420
gcttgggccg agcggggatc ttggccagtg gtaattaaac cccaggcttc gcacgacaca    480
gacagtgtta cattctgcgc cgatcaggga gaattattag agtcgtttga tcaattgttc    540
ggcactgtga accaattggg tgaacgcaat aatgcagtgc tggctcagcg tctgttggtt    600
ggtcccgagt actttatcaa cggagtttct ggacatggca aacacctgat tacagagatt    660
tggcgtgcag acaagctgcc cgcaccggac gggggttgga tatacgaccg ggccgtgctg    720
tttgacccga tcagtcccga gatgcaggag attgtccgct acgtgcatgg agtattagat    780
gcccttggca tccgctatgg tgcgaaccat acagagctga tcgtaacggc tgatggccca    840
acactgatag aatgtgcctc ccgtttactc gggtggctgc atagacctgc agcgaactat    900
gcggttggcg catcacaact tgacttggtc ggtaaacttg tacgggaagg ggaaagcgct    960
atagatgata tactgcaaac ttggcaacct caccgctacg cattgtggca agtccaattc   1020
atatcgaatc aagagggagt agtggctcgg agttcgtacg acgaacttct taaaacgttg   1080
aaatccaatg cctggttgca acgggctccg aaggaaggcg ataccgtagt caagacagtc   1140
gacctgttca gctcgcccgg aatagtcttt atgtcacacg cagacggtaa tgttctgcac   1200
gacgattatc ggacggtccg ggaatgggag cgtacctcgc gcctgttctc ggtgcagggt   1260
ggtggtggat caggggggtgg gggttcaggc ggtggcggat ccggcggggg tggttccatg   1320
gcacactatc caccttccaa ggatcaattg aatgaattga tccaggaagt taaccaatgg   1380
gctatcacta atggattatc catgtatcct cctaaattcg aggagaaccc atcaaatgca   1440
tcggtgtcac cagtaactat ctatccaacc ccaattccta ggaaatgttt tgatgaggcc   1500
gttcaaatac aaccggtatt caatgaatta tacgcccgta ttacccaaga tatggcccaa   1560
cctgattctt atttacataa aacaactgaa gcgttagctc tatcagattc cgagtttact   1620
ggaaaactgt ggtctctata ccttgctacc ttaaaatctg cacagtacaa aaagcagaat   1680
tttaggctag gtatatttag atcacagtat ttgattgata agaaaaaggg tactgaacag   1740
attaagcaag tcctgtttag tacattctca gtggaatttg caggccttag cgagaaagtt   1800
gatagattgc actcttattt aaatagggca aacaagtacg atcctaaagg accaatttat   1860
aatgatcaaa atatggtcat ttctgattca ggataccttt tgtctaaggc attggccaaa   1920
gctgtggaat cgtataagtc acaacaaagt tcttctacaa ctagtgatcc tattgtcgca   1980
ttcattgtgc aaagaaacat cagacatgtg tttactcaaa aggtcttgga attgaatctg   2040
ttggaaaaat tcggtaccaa atctgttagg ttgacgtttg atgatgttaa cgataaattg   2100
ttcattgatg ataaaacggg aaagcttttc attagggaca cagagcagga aatagcggtg   2160
gtttattacg taacgggtta cacaaccact gattacacgt ccgaaaagga ctgggaggca   2220
```

```
agactattcc tcgaaaaaag tttcgcaata aaggccccag atttactcac tcaattatct   2280

ggctccaaga aaattcagca attgttgaca gatgagggcg tattaggtaa atacatctcc   2340

gatgctgaga aaaagagtag tttgttaaaa acttttgtca aaatatatcc cttggatgat   2400

acgaagcttg gcagggaagg caagaggctg gcattaagtg agccctctaa atacgtgtta   2460

aaaccacagc gggaaaatgg cggaaacaat gtttataaag aaaatattcc taatttttg    2520

aaaggtatcg aagaacgtca ctgggatgca tatattctca tggagttgat tgaaccagag   2580

ttgaatgaaa ataatattat attacgtgat aacaaatctt acaacgaacc aatcatcagt   2640

gaactaggag attatggttg cgttctattt aacgacgagc aagtttttatc gaacgaattt   2700

agtggctcat tactaagatc caaatttaat acttcaaatg aaggtggagt ggcggcagga   2760

ttcggatgtt tggacagtat tattctttac tag                                2793
```

<210> SEQ ID NO 14
<211> LENGTH: 2793
<212> TYPE: DNA
<213> ORGANISM: Artificial Sequence
<220> FEATURE:
<223> OTHER INFORMATION: GHKS-2

<400> SEQUENCE: 14

```
atgacgcagg ccaaggaaaa catcttagtt gtggtcgatg gctactcctc aggcagtcag     60

ttgcctaccc tgatggcgga atccggctgg aagtgtgttc atgtctcgtc ctcggctaac    120

cccccggagt attacctgcg tacataccat aaggatgagt acatagctca ctttgagtat    180

caaggtgata tacagtcact tgctagtgct gttgaggcgt ggcatcccgc cgcagttctt    240

cctggtacga aaagtggagt tattgtcgct gatttactgg cggctgcttt gcaattgcca    300

ggcaatgacc cgtcgacctc cctggcgaga cgcgacaaat atacgatgca tgagtcattg    360

aaagcggtgg gacttcggag tatggaccat ttccttgccg tcgatcgtga tgctttatca    420

gcttgggccg agcggggatc ttggccagtg gtaattaaac cccaggcttc gcacgacaca    480

gacagtgtta cattctgcgc cgatcaggga gaattattag agtcgtttga tcaattgttc    540

ggcactgtga accaattggg tgaacgcaat aatgcagtgc tggctcagcg tctgttggtt    600

ggtcccgagt actttatcaa cggagtttct ggacatggca aacacctgat tacagagatt    660

tggcgtgcag acaagctgcc cgcaccggac gggggttgga tatacgaccg ggccgtgctg    720

tttgacccga tcagtcccga gatgcaggag attgtccgct acgtgcatgg agtattagat    780

gcccttggca tccgctatgg tgcgaaccat acagagctga tcgtaacggc tgatggccca    840

acactgatag aatgtgcctc ccgtttactc gggtggctgc atagacctgc agcgaactat    900

gcggttggcg catcacaact tgacttggtc ggtaaacttg tacgggaagg ggaaagcgct    960

atagatgata tactgcaaac ttggcaacct caccgctacg cattgtggca agtccaattc   1020

atatcgaatc aagagggagt agtggctcgg agttcgtacg acgaacttct taaaacgttg   1080

aaatccaatg cctggttgca acgggctccg aaggaaggcg ataccgtagt caagacagtc   1140

gacctgttca gctcgcccgg aatagtcttt atgtcacacg cagacggtaa tgttctgcac   1200

gacgattatc ggacggtccg ggaatgggag cgtacctcgc gcctgttctc ggtgcagggt   1260

ggtgggggat ctgaggctgc ggctaaagag gcggcagcaa aggaggaggg cggaagcatg   1320

gcacactatc caccttccaa ggatcaattg aatgaattga tccaggaagt taaccaatgg   1380

gctatcacta atggattatc catgtatcct cctaaattcg aggagaaccc atcaaatgca   1440
```

```
tcggtgtcac cagtaactat ctatccaacc ccaattccta ggaaatgttt tgatgaggcc   1500

gttcaaatac aaccggtatt caatgaatta tacgcccgta ttacccaaga tatggcccaa   1560

cctgattctt atttacataa aacaactgaa gcgttagctc tatcagattc cgagtttact   1620

ggaaaactgt ggtctctata ccttgctacc ttaaaatctg cacagtacaa aaagcagaat   1680

tttaggctag gtatatttag atcacagtat ttgattgata agaaaaaggg tactgaacag   1740

attaagcaag tcctgtttag tacattctca gtggaatttg caggccttag cgagaaagtt   1800

gatagattgc actcttattt aaatagggca aacaagtacg atcctaaagg accaatttat   1860

aatgatcaaa atatggtcat ttctgattca ggataccttt tgtctaaggc attggccaaa   1920

gctgtggaat cgtataagtc acaacaaagt tcttctacaa ctagtgatcc tattgtcgca   1980

ttcattgtgc aaagaaacat cagacatgtg tttactcaaa aggtcttgga attgaatctg   2040

ttggaaaaat tcggtaccaa atctgttagg ttgacgtttg atgatgttaa cgataaattg   2100

ttcattgatg ataaaacggg aaagcttttc attagggaca cagagcagga aatagcggtg   2160

gtttattacg taacgggtta cacaaccact gattacacgt ccgaaaagga ctgggaggca   2220

agactattcc tcgaaaaaag tttcgcaata aaggccccag atttactcac tcaattatct   2280

ggctccaaga aaattcagca attgttgaca gatgagggcg tattaggtaa atacatctcc   2340

gatgctgaga aaaagagtag tttgttaaaa acttttgtca aaatatatcc cttggatgat   2400

acgaagcttg gcagggaagg caagaggctg gcattaagtg agccctctaa atacgtgtta   2460

aaaccacagc gggaaaatgg cggaaacaat gtttataaag aaaatattcc taatttttg    2520

aaaggtatcg aagaacgtca ctgggatgca tatattctca tggagttgat tgaaccagag   2580

ttgaatgaaa ataatattat attacgtgat aacaaatctt acaacgaacc aatcatcagt   2640

gaactaggag attatggttg cgttctattt aacgacgagc aagttttatc gaacgaattt   2700

agtggctcat tactaagatc caaatttaat acttcaaatg aaggtggagt ggcggcagga   2760

ttcggatgtt tggacagtat tattctttac tag                                2793
```

<210> SEQ ID NO 15
<211> LENGTH: 861
<212> TYPE: DNA
<213> ORGANISM: Artificial Sequence
<220> FEATURE:
<223> OTHER INFORMATION: PPK

<400> SEQUENCE: 15

```
atgccaatgg ttgctgcagt tgagttcgcc aaaagtccgg ccgaagtact gagggttgga     60

tcggggtttt cgctggcagg cgtggatccc gaatccacac ccggctacac cggtgtgaaa    120

gctgatggca aggcgttgct tgccgcgcag gacgcgcggc tggcggaact gcaggaaaag    180

ctcttcgccg aaggaaagtt cggcaacccc aaacggctcc tgctcatcct tcaggccatg    240

gatactgcgg gcaagggcgg cattgtcagc cacgttgttg gcgccatgga cccgcaaggc    300

gtacaactga ccgccttcaa agcgcctacg gacgaggaaa agtcgcacga cttcctctgg    360

agaatcgaaa aacaagtccc tgccgccgga atggtggggg tgttcgaccg ctcgcagtac    420

gaagacgtgc tgatccaccg tgtccatggc tgggcggacg ctgccgaact ggagcgccgg    480

tacgccgcga tcaacgactt tgagtcacgc ctgaccgagc agggaaccac catcgtcaag    540

gtcatgctca atatcagcaa ggacgaacag aaaaagcgtt tgatcgcccg gttggacgat    600

cccagcaagc actggaaata cagtcgcggc gacctcgcgg aacgtgcgta ctgggatgac    660

tacatggacg cctacagcgt tgccttcgag aagacctcca cagagattgc tccttggcac    720
```

gtggtgccgg caaacaagaa gtggtacgca cgcatcgcag tccagcaact gctgctggat 780
gccctcggcg gtttgcagct ggactggccc aaagctgact tcgatgtcgc cgctgagcgc 840
gccctcgtgg tggaatccta g 861

<210> SEQ ID NO 16
<211> LENGTH: 645
<212> TYPE: DNA
<213> ORGANISM: Artificial Sequence
<220> FEATURE:
<223> OTHER INFORMATION: ADK

<400> SEQUENCE: 16
atgcgtatca ttctgcttgg cgctccgggc gcggggaaag ggactcaggc tcagttcatc 60
atggagaaat atggtattcc gcaaatctcc actggcgata tgctgcgtgc tgcggtcaaa 120
tctggctccg agctgggtaa acaagcaaaa gacattatgg atgctggcaa actggtcacc 180
gacgaactgg tgatcgcgct ggttaaagag cgcattgctc aggaagactg ccgtaatggt 240
ttcctgttgg acggcttccc gcgtaccatt ccgcaggcag acgcgatgaa agaagcgggc 300
atcaatgttg attacgttct ggaattcgac gtaccggacg aactgatcgt tgaccgtatc 360
gtcggtcgcc gcgttcatgc gccgtctggt cgtgtttatc acgttaaatt caatccgccg 420
aaagtagaag gcaaagacga cgttaccggt gaagaactga ctacccgtaa agatgatcag 480
gaagagaccg tacgtaaacg tctggttgaa taccatcaga tgacagcacc gctgatcggc 540
tactactcca aagaagcaga agcgggtaat accaaatacg cgaaagttga cggcaccaag 600
ccggttgctg aagttcgcgc tgatctggaa aaaatcctcg gctaa 645

<210> SEQ ID NO 17
<211> LENGTH: 20
<212> TYPE: PRT
<213> ORGANISM: Artificial Sequence
<220> FEATURE:
<223> OTHER INFORMATION: Linking peptide

<400> SEQUENCE: 17

Gly Gly Gly Gly Ser Gly Gly Gly Gly Ser Gly Gly Gly Gly Ser Gly
1 5 10 15

Gly Gly Gly Ser
20

<210> SEQ ID NO 18
<211> LENGTH: 20
<212> TYPE: PRT
<213> ORGANISM: Artificial Sequence
<220> FEATURE:
<223> OTHER INFORMATION: Linking peptide

<400> SEQUENCE: 18

Gly Gly Gly Gly Ser Glu Ala Ala Ala Lys Glu Ala Ala Ala Lys Gly
1 5 10 15

Gly Gly Gly Ser
20

MUTANT ENZYME, USE THEREOF AND PROCESS FOR PREPARING TRIPEPTIDE BY USING ENZYMATIC METHOD

This application claims the priority of Chinese Patent Application No. 202011231194.8, filed with the China National Intellectual Property Administration on Nov. 6, 2020, and titled with "MUTANT ENZYME, USE THEREOF AND PROCESS FOR PREPARING TRIPEPTIDE BY USING ENZYMATIC METHOD", which is hereby incorporated by reference in its entirety.

FIELD

The present disclosure relates to the field of biochemical technology, in particular to a mutant enzyme, use thereof and a method for producing prezatide by enzymatic catalysis method.

BACKGROUND

Prezatide (glycyl-L-histidyl-L-lysine, GHK) is a natural tripeptide compound (Gly-L-His-L-Lys) composed of glycine, L-histidine and L-lysine, with a molecular formula of $C_{14}H_{24}N_6O_4$ and a molecular weight of 340. Prezatide can effectively complex with an equivalent amount of copper to form copper peptide. Copper, as an important element in living organisms, participates in important physiological functions such as cellular respiration, anti-oxidation, detoxification, blood coagulation, and melanin and connective tissue formation in living organisms. Prezatide can effectively complex and transport copper element to exert corresponding effects. For example, the complexed prezatide copper can effectively stimulate biosynthesis of collagen in fibroblasts, thereby promoting rapid healing of wounds. Prezatide copper can also effectively prevent neurotransmission of acetylcholine, thereby exerting effects of relaxing muscles and improving dynamic wrinkles. Prezatide is now widely used as a cosmetic additive.

Methods for producing prezatide on the market are mainly separation method and chemical synthesis method. Since prezatide exists in many animals, it was initially discovered and prepared through extraction of and separation from a large amount of animal viscera aqueous solution. The tedious separation procedure and extremely low yield of this method make it impossible to realize large-scale production. The chemical synthesis method is a common method for the industrial production of prezatide at present. Similar to the chemical synthesis of other peptides, the chemical production process of prezatide inevitably requires cumbersome steps such as selective protection of functional groups, condensation and deprotection, which greatly increases production cost and results in racemization of some chiral functional groups, thereby reducing product quality.

Unlike glutathione (GSH), though prezatide (GHK) also exists in many animals, no corresponding amino acid ligase has been found so far to produce GHK. It may be generated through graded degradation of peptides or proteins in vivo. However, there are a large number of short peptide synthetases in nature, such as L-amino acid ligase (Lal, EC 6.3.2.49), which are found to be able to connect a variety of amino acids directly or through modification. However, it is detected by HPLC in the present disclosure that Lal only has very low glycine and L-histidine ligase activity (maximum conversion rate of less than 1%), which thus cannot be used for scale-up production. Moreover, glutathione synthase (gshB, EC 6.3.2.3) is also widely reported that it can catalyze the linking of specific dipeptides and amino acids to form tripeptide products, and its substrates are also diverse. However, as verified by the practice of the present disclosure, gshB enzyme has no ability for synthesizing glycine-L-histidine and L-lysine. Therefore, how to obtain corresponding amino acid ligases to produce GHK is the most critical issue.

SUMMARY

In view of this, an object of the present disclosure is to provide a mutant enzyme that can achieve glycine and L-histidine ligase activity, and realize the ability for synthesizing dipeptide glycine-L-histidine and L-lysine, thereby efficiently producing prezatide by enzymatic method.

Another object of the present disclosure is to provide use of the above mutant enzyme in the production of prezatide.

Another object of the present disclosure is to provide a method for producing prezatide using the above mutant enzyme.

To achieve the above objects, the present disclosure provides the following technical solutions:

A mutant enzyme, wherein it comprises glycine and L-histidine ligase GHS and tripeptide ligase HKS, or is a fusion enzyme of the two;

wherein, the glycine and L-histidine ligase GHS is an enzyme with mutations on sites T244I, S290L, G292W, E84K, A158H, and G159D of a wild-type L-amino acid ligase Lal, and the tripeptide ligase HKS is an enzyme with mutations on sites V150F, S153E, E228I, N230H, D233T, R285V, D130Q, E146L, N148S, G387, and I445D of a wild-type glutathione synthase gshB.

Aiming at the defect of lacking amino acid ligase to produce GHK at present, the present disclosure performs site mutation modification on the basis of the existing L-amino acid ligase (Lal, EC 6.3.2.49) and glutathione synthase (gshB, EC 6.3.2.3), which can achieve the glycine and L-histidine ligase activity and the ability for synthesizing dipeptide glycine-L-histidine and L-lysine, and realize the purpose of producing prezatide by enzymatic catalysis method in one step.

In addition, in the present disclosure, the two mutant enzymes are further fused via a linking peptide to construct a bifunctional enzyme MKS that links glycine, L-histidine and L-lysine at once, thereby realizing convenient production of prezatide with a high yield. In a specific embodiment of the present disclosure, the linking peptide has a sequence set forth in SEQ ID No. 17 or 18.

In the present disclosure, L-amino acid ligase (Lal, EC 6.3.2.49) is derived from *Pseudomonas syringae*; gshB enzyme (EC 6.3.2.3) is derived from *Saccharomyces cerevisiae* and belongs to PF02955 & PF02951 enzyme family; PPK (EC 2.7.4.1) is derived from *Paenarthrobacter aurescens* and belongs to PF03976 enzyme family; and ADK (EC 2.7.4.3) is derived from *Escherichia coli* and belongs to PF05191 enzyme family.

The use of the mutant enzyme provided by the present disclosure can realize the catalytic linkage of glycine, L-histidine and L-lysine to produce prezatide in one step, which has a yield of 62-91% and a purity of more than 90%. The product has few impurities, and the reaction and purification process is simple and convenient. Based on such excellent technical effect, the present disclosure provides use of the mutant enzyme in catalyzing glycine, L-histidine and L-lysine to produce prezatide or in the manufacture of an enzyme preparation for catalyzing glycine, L-histidine and L-lysine to produce prezatide. Preferably, the enzyme preparation is a host cell expressing the mutant enzyme, an enzyme solution of the mutant enzyme or an immobilized enzyme of the mutant enzyme.

According to the use, the present disclosure provides a method for producing prezatide by enzymatic catalysis method, comprising subjecting reaction raw materials of glycine, L-histidine, L-lysine and ATP or salt thereof to enzymatic catalysis reaction with the mutant enzyme in a reaction medium within a pH range of the mutant enzyme of the present disclosure to produce prezatide.

During the reaction, the pH of the system is maintained within the pH range of the mutant enzyme. In a specific embodiment of the present disclosure, the pH range of the mutant enzyme is 6.5-9.0, but it does not exclude other pH ranges that enable the mutant enzyme to exert its functions. Preferably, the ATP salt is ATP sodium salt, such as adenosine disodium triphosphate, which can also provide ATP.

Preferably, the reaction medium is a buffer solution. In a specific embodiment of the present disclosure, the buffer solution is Tris-HCl.

In addition, polyphosphate kinase (PPK, EC 2.7.4.1) can utilize cheap polyphosphoric acid as a raw material to convert adenosine diphosphate ADP into adenosine triphosphate ATP, and adenylate kinase (ADK, EC 2.7.4.3) can realize the interconversion of three adenosine phosphates (AMP, ADP and ATP). The combined use of these two enzymes or the fusion expression of the two enzymes (PPK-ADK/ADK-PPK) can not only reduce the production cost of enzyme fermentation, but also effectively accelerate the ATP regeneration. Therefore, the method of the present disclosure further comprises adding reaction raw materials of PPK and ADK or a fusion protein of the two, polyphosphoric acid, magnesium chloride and potassium chloride (magnesium chloride and potassium chloride are used for ATP regeneration). The schematic diagram of the specific reaction principle is shown in FIG. 1.

The mutant enzyme of the present disclosure, PPK and ADK or a fusion enzyme of the two (PPK-ADK/ADK-PPK) can participate in an enzymatic catalysis reaction in the forms of a host cell expressing the enzyme, an enzyme solution of the enzyme or an immobilized enzyme of the enzyme.

Similar to most of the reactions, the present disclosure further comprises a purification step selected from the group consisting of removing protein impurities, removing residual reaction raw materials, desalting, removing phosphoric acid, crystallization and a combination thereof. The specific purification step is selected according to the actual situation. Specifically, protein impurities are removed by acidification treatment, salt is removed by reverse osmosis, impurities containing phosphoric acid are removed by anion exchange resin, and crystallization is performed with ethanol aqueous solution for purification, preferably at pure water: ethanol of (1-3): 1 v/v.

It can be known from the above technical solutions that through modification, the present disclosure enables Lal enzyme to achieve the glycine and L-histidine ligase activity and allows gshB enzyme to realize the ability for synthesizing dipeptide glycine-L-histidine and L-lysine. On this basis, GHS enzyme and HKS enzyme are further fused together via a linking peptide to construct a bifunctional enzyme GHKS that links glycine, L-histidine and L-lysine at once, thereby realizing convenient production of prezatide with a high yield. Further, the large amount of adenosine triphosphate required in the enzymatic catalysis reaction can be cyclically regenerated by polyphosphokinase PPK, thereby greatly reducing the amount of ATP used.

DETAILED DESCRIPTION

Figures 1, 2:
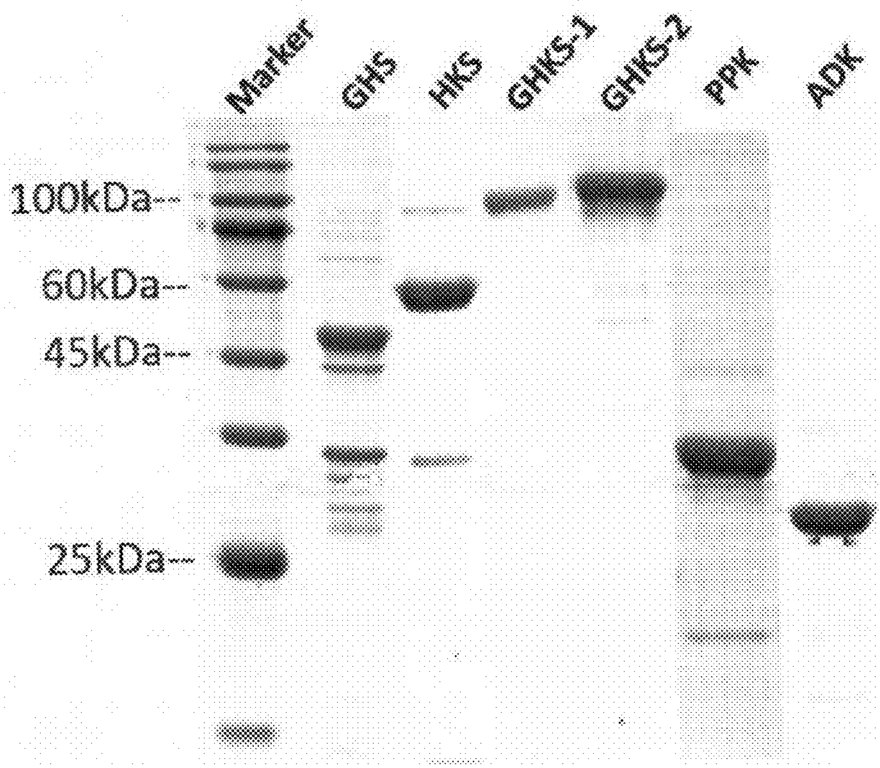
FIG. 1 shows the schematic diagram of the reaction principle of the present disclosure.
FIG. 2 shows the SDS-PAGE gel image of the purified enzyme.

The present disclosure discloses a mutant enzyme and use thereof and a method for producing prezatide by enzymatic catalysis method. Those skilled in the art can learn from the content herein and appropriately improve the process parameters for realization. In particular, it should be noted that all similar replacements and modifications are apparent to those skilled in the art, which are all considered to be included in the present disclosure. The mutant enzyme and use thereof and the related method of the present disclosure have been described through preferred embodiments, and those skilled in the art can apparently make modifications or appropriate changes and combination to the mutant enzyme and use thereof and the related method herein without departing from the content, spirit and scope of the present disclosure to realize and apply the technology of the present disclosure.

The steps of the method described in the present disclosure are intended to clearly describe the core reaction route, and do not limit whether the whole reaction is carried out by one-step method or multi-step method.

In a specific embodiment of the present disclosure, all enzymes used can be artificially synthesized according to their sequences. The sequences of the enzymes mentioned in the present disclosure are summarized as shown in Table 1:

TABLE 1

| Abbreviation | Sequence number | Amino acid sequence of enzyme |
|---|---|---|
| Lal | SEQ ID No. 1 | MTQAKENILVVVDGYSSGSQLPTLMAESGWKCVHV SSSANPPEYYLRTYHKDEYIAHFEYQGDIQSLASAVE AWHPAAVLPGTESGVIVADLLAAALQLPGNDPSTSLA RRDKYTMHESLKAVGLRSMDHFLAVDRDALSAWAE RGSWPVVIKPQASAGTDSVTFCADQGELLESFDQLF GTVNQLGERNNAVLAQRLLVGPEYFINGVSGHGKHL ITEIWRADKLPAPDGGWIYDRAVLFDPTSPEMQEIVR YVHGVLDALGIRYGANHTELIVTADGPTLIECASRLS GGLHRPAANYAVGASQLDLVGKLVREGESAIDDILQT WQPHRYALWQVQFISNQEGVVARSSYDELLKTLKSN AWLQRAPKEGDTVVKTVDLFSSPGIVFMSHADGNVL HDDYRTVREWERTSRLFSVQ |

TABLE 1-continued

| Abbreviation | Sequence number | Amino acid sequence of enzyme |
|---|---|---|
| GHS | SEQ ID No. 2 | MTQAKENILVVVDGYSSGSQLPTLMAESGWKCVHV<br>SSSANPPEYYLRTYHKDEYIAHFEYQGDIQSLASAVE<br>AWHPAAVLPGT**K**SGVIVADLLAAALQLPGNDPSTSLA<br>RRDKYTMHESLKAVGLRSMDHFLAVDRDALSAWAE<br>RGSWPVVIKPQAS**HD**TDSVTFCADQGELLESFDQLF<br>GTVNQLGERNNAVLAQRLLVGPEYFINGVSGHGKHL<br>ITEIWRADKLPAPDGGWIYDRAVLFDP**I**SPEMQEIVRY<br>VHGVLDALGIRYGANHTELIVTADGPTLIECASRL**L**G<br>**W**LHRPAANYAVGASQLDLVGKLVREGESAIDDILQT<br>WQPHRYALWQVQFISNQEGVVARSSYDELLKTLKSN<br>AWLQRAPKEGDTVVKTVDLFSSPGIVFMSHADGNVL<br>HDDYRTVREWERTSRLFSVQ |
| gshB | SEQ ID No. 3 | MAHYPPSKDQLNELIQEVNQWAITNGLSMYPPKFEE<br>NPSNASVSPVTIYPTPIPRKCFDEAVQIQPVFNELYARI<br>TQDMAQPDSYLHKTTEALALSDSEFTGKLWSLYLAT<br>LKSAQYKKQNFRLGIFRSDYLIDKKKGTEQIKQVEFN<br>TVSVSFAGLSEKVDRLHSYLNRANKYDPKGPIYNDQ<br>NMVISDSGYLLSKALAKAVESYKSQQSSSTTSDPIVAF<br>IVQRNERNVFDQKVLELNLLEKFGTKSVRLTFDDVN<br>DKLFIDDKTGKLFIRDTEQEIAVVYYRTGYTTTDYTSE<br>KDWEARLFLEKSFAIKAPDLLTQLSGSKKIQQLLTDE<br>GVLGKYISDAEKKSSLLKTFVKIYPLDDTKLGREGKR<br>LALSEPSKYVLKPQREGGGNNVYKENIPNFLKGIEER<br>HWDAYILMELIEPELNENNIILRDNKSYNEPIISELGIY<br>GCVLFNDEQVLSNEFSGSLLRSKFNTSNEGGVAAGFG<br>CLDSIILY |
| HKS | SEQ ID No. 4 | MAHYPPSKDQLNELIQEVNQWAITNGLSMYPPKFEE<br>NPSNASVSPVTIYPTPIPRKCFDEAVQIQPVFNELYARI<br>TQDMAQPDSYLHKTTEALALSDSEFTGKLWSLYLAT<br>LKSAQYKKQNFRLGIFRS**Q**YLIDKKKGTEQIKQV**L**F**S**<br>T**F**SV**E**FAGLSEKVDRLHSYLNRANKYDPKGPIYNDQ<br>NMVISDSGYLLSKALAKAVESYKSQQSSSTTSDPIVAF<br>IVQRN**I**R**H**VF**T**QKVLELNLLEKFGTKSVRLTFDDVND<br>KLFIDDKTGKLFIRDTEQEIAVVYY**V**TGYTTTDYTSE<br>KDWEARLFLEKSFAIKAPDLLTQLSGSKKIQQLLTDE<br>GVLGKYISDAEKKSSLLKTFVKIYPLDDTKLGREGKR<br>LALSEPSKYVLKPQRE**N**GGNNVYKENIPNFLKGIEER<br>HWDAYILMELIEPELNENNIILRDNKSYNEPIISELG**D**<br>YGCVLFNDEQVLSNEFSGSLLRSKFNTSNEGGVAAGF<br>GCLDSIILY |
| GHKS-1 | SEQ ID No. 5 | MTQAKENILVVVDGYSSGSQLPTLMAESGWKCVHV<br>SSSANPPEYYLRTYHKDEYIAHFEYQGDIQSLASAVE<br>AWHPAAVLPGT**K**SGVIVADLLAAALQLPGNDPSTSLA<br>RRDKYTMHESLKAVGLRSMDHFLAVDRDALSAWAE<br>RGSWPVVIKPQAS**HD**TDSVTFCADQGELLESFDQLF<br>GTVNQLGERNNAVLAQRLLVGPEYFINGVSGHGKHL<br>ITEIWRADKLPAPDGGWIYDRAVLFDP**I**SPEMQEIVRY<br>VHGVLDALGIRYGANHTELIVTADGPTLIECASRL**L**G<br>**W**LHRPAANYAVGASQLDLVGKLVREGESAIDDILQT<br>WQPHRYALWQVQFISNQEGVVARSSYDELLKTLKSN<br>AWLQRAPKEGDTVVKTVDLFSSPGIVFMSHADGNVL<br>HDDYRTVREWERTSRLFSVQ*GGGGSGGGGSGGGGSG*<br>*GGGS*MAHYPPSKDQLNELIQEVNQWAITNGLSMYPP<br>KFEENPSNASVSPVTIYPTPIPRKCFDEAVQIQPVFNEL<br>YARITQDMAQPDSYLHKTTEALALSDSEFTGKLWSLY<br>LATLKSAQYKKQNFRLGIFRS**Q**YLIDKKKGTEQIKQV<br>**L**F**S**T**F**SV**E**FAGLSEKVDRLHSYLNRANKYDPKGPIYN<br>DQNMVISDSGYLLSKALAKAVESYKSQQSSSTTSDPI<br>VAFIVQRN**I**R**H**VF**T**QKVLELNLLEKFGTKSVRLTFDD<br>VNDKLFIDDKTGKLFIRDTEQEIAVVYY**V**TGYTTTDY<br>TSEKDWEARLFLEKSFAIKAPDLLTQLSGSKKIQQLLT<br>DEGVLGKYISDAEKKSSLLKTFVKIYPLDDTKLGREG<br>KRLALSEPSKYVLKPQRE**N**GGNNVYKENIPNFLKGIE<br>ERHWDAYILMELIEPELNENNIILRDNKSYNEPIISELG<br>**D**YGCVLFNDEQVLSNEFSGSLLRSKFNTSNEGGVAA<br>GFGCLDSIILY |

TABLE 1-continued

| Abbreviation | Sequence number | Amino acid sequence of enzyme |
|---|---|---|
| GHKS-2 | SEQ ID No. 6 | MTQAKENILVVVDGYSSGSQLPTLMAESGWKCVHV<br>SSSANPPEYYLRTYHKDEYIAHFEYQGDIQSLASAVE<br>AWHPAAVLPGT**K**SGVIVADLLAAALQLPGNDPSTSLA<br>RRDKYTMHESLKAVGLRSMDHFLAVDRDALSAWAE<br>RGSWPVVIKPQAS**HD**TDSVTFCADQGELLESFDQLF<br>GTVNQLGERNNAVLAQRLLVGPEYFINGVSGHGKHL<br>ITEIWRADKLPAPDGGWIYDRAVLFDP**I**SPEMQEIVRY<br>VHGVLDALGIRYGANHTELIVTADGPTLIECASRL**L**G<br>**W**LHRPAANYAVGASQLDLVGKLVREGESAIDDILQT<br>WQPHRYALWQVQFISNQEGVVARSSYDELLKTLKSN<br>AWLQRAPKEGDTVVKTVDLFSSPGIVFMSHADGNVL<br>HDDYRTVREWERTSRLFSVQ*GGGGSEAAAKEAAAKG*<br>*GGGS*MAHYPPSKDQLNELIQEVNQWAITNGLSMYPP<br>KFEENPSNASVSPVTIYPTPIPRKCFDEAVQIQPVFNEL<br>YARITQDMAQPDSYLHKTTEALALSDSEFTGKLWSLY<br>LATLKSAQYKKQNFRLGIFRS**Q**YLIDKKKGTEQIKQV<br>**L**F**S**T**F**SV**E**FAGLSEKVDRLHSYLNRANKYDPKGPIYN<br>DQNMVISDSGYLLSKALAKAVESYKSQQSSSTTSDPI<br>VAFIVQRN**I**R**H**VF**T**QKVLELNLLEKFGTKSVRLTFDD<br>VNDKLFIDDKTGKLFIRDTEQEIAVVYY**V**TGYTTTDY<br>TSEKDWEARLFLEKSFAIKAPDLLTQLSGSKKIQQLLT<br>DEGVLGKYISDAEKKSSLLKTFVKIYPLDDTKLGREG<br>KRLALSEPSKYVLKPQRE**N**GGNNVYKENIPNFLKGIE<br>ERHWDAYILMELIEPELNENNIILRDNKSYNEPIISELG<br>**D**YGCVLFNDEQVLSNEFSGSLLRSKFNTSNEGGVAA<br>GFGCLDSIILY |
| PPK | SEQ ID No. 7 | MPMVAAVEFAKSPAEVLRVGSGFSLAGVDPESTPGYT<br>GVKADGKALLAAQDARLAELQEKLFAEGKFGNPKR<br>LLLILQAMDTAGKGGIVSHVVGAMDPQGVQLTAFKA<br>PTDEEKSHDFLWRIEKQVPAAGMVGVFDRSQYEDVL<br>IHRVHGWADAAELERRYAAINDFESRLTEQGTTIVKV<br>MLNISKDEQKKRLIARLDDPSKHWKYSRGDLAERAY<br>WDDYMDAYSVAFEKTSTEIAPWHVVPANKKWYARI<br>AVQQLLLDALGGLQLDWPKADFDVAAERALVVES |
| ADK | SEQ ID No. 8 | MRIILLGAPGAGKGTQAQFIMEKYGIPQISTGDMLRA<br>AVKSGSELGKQAKDIMDAGKLVTDELVIALVKERIAQ<br>EDCRNGFLLDGFPRTIPQADAMKEAGINVDYVLEFD<br>VPDELIVDRIVGRRVHAPSGRVYHVKFNPPKVEGKD<br>DVTGEELTTRKDDQEETVRKRLVEYHQMTAPLIGYY<br>SKEAEAGNTKYAKVDGTKPVAEVRADLEKILG |

In Table 1, GHKS-1 and GHKS-2 are two fusion enzymes (GHS-HKSs with different linking peptides) provided by the present disclosure, bold and underlined amino acids indicate mutation sites and mutated amino acids, and italic and underlined sequences are linking peptide sequences.

The above enzymes can also be obtained by cell transformation with recombinant plasmids constructed with their coding genes respectively, for example:

The gene fragments of ADK, gshB and PPK were amplified with chromosomes of *Escherichia coli* K12, *Saccharomyces cerevisiae* (ATCC 204508) and *Paenarthrobacter aurescens* TC1 purchased from ATCC as templates by PCR using the primers in Table 2, subjected to enzyme digestion using the Nde I/Xho I purchased from NEB Company, and connected to a pET28a plasmid (purchased from Addgene) digested with the same enzyme. Then the plasmid was transformed into *E. coli* DH5a cells (purchased from Tsingke Biotechnology), and verified by colony PCR and gene sequencing. Lal gene fragment was synthesized by Anhui General Biology Co., Ltd., and subcloned into a pET28a plasmid. Then multi-site mutant enzyme genes GHS and HKS were constructed with Lal and gshB genes as templates using the mutation primers in Table 2 (by conventional PCR amplification). The above GHS, HKS, PPK and ADK plasmids constructed with the pET-28a vector were transferred into *E. coli* BL21 (DE3) (purchased from Anhui General Biology Co., Ltd.) strains, which were then cultured in a small-scale in 5 ml of LB culture medium containing 50 μM Kanamycin at 37° C. When the cells grew to an OD value of 0.5-0.8, 0.5 mM isopropyl-β-D-thiogalactopyranoside (IPTG) was added to induce protein expression at 37° C. for 3 h. Finally the cells were collected, disrupted by freeze-thaw method, and centrifuged at high speed, and the collected supernatant was subjected to sodium dodecyl sulfate polyacrylamide gel electrophoresis (SDS-PAGE) to confirm the protein expression. The strains with correct protein expression were cultured step by step in a 5 liter fermenter to be induced for expression under the condition of 1.0 mM IPTG at 37° C. for 4 h, and wet cells were collected to be 35-55 g. Then after the cells and an appropriate amount of Tris·HCl buffer solution (25 mM, pH=8.0) were mixed evenly, the cells were crushed with a high-pressure crusher at low temperature and centrifuged at high speed to remove the cell wall to obtain an enzyme solution, which was stored in a refrigerator at 4° C. for later use. The LB culture medium was composed of 1% tryptone, 0.5% yeast powder, 1% NaCl, 1% dipotassium phosphate, 1% dipotassium phosphate and 5% glycerol.

TABLE 2

| Primer name | Primer sequence |
|---|---|
| Information of primers for construction of Lal mutant: mutation at glycine binding site (the bold and underlined represent mutation sites) | |
| T244IForward | CTGTTTGACCCG**ATC**AGTCCCGAGATGCAG |
| T244IReverse | CTGCATCTCGGGACT**GAT**CGGGTCAAACAG |
| S290LForward | GTGCCTCCCGTTTA**CTC**GGG**TGG**CTGCATAGAC |
| S290LReverse | GTCTATGCAG**CCA**CCC**GAG**TAAACGGGAGGCAC |
| G292WForward | GTGCCTCCCGTTTA**CTC**GGG**TGG**CTGCATAGAC |
| G292WReverse | GTCTATGCAG**CCA**CCC**GAG**TAAACGGGAGGCAC |
| Information of primers for construction of Lal mutant: mutation at L-histidine binding site | |
| E84KForward | CTTCCTGGTACG**AAA**AGTGGAGTTATTGTC |
| E84KReverse | GACAATAACTCCACT**TTT**CGTACCAGGAAG |
| A158HForward | CAGGCTTCG**CACGAC**ACAGACAGTGTTACATTC |
| A158HReverse | GAATGTAACACTGTCTGT**GTCGTG**CGAAGCCTG |
| G159DForward | CAGGCTTCG**CACGAC**ACAGACAGTGTTACATTC |
| G159DReverse | GAATGTAACACTGTCTGT**GTCGTG**CGAAGCCTG |
| Information of primers for construction of gshB mutant: mutation at glycine-L-histidine binding site | |
| V150FForward | GATTAAGCAAGTC**CTG**TTT**AGT**ACA**TTC**TCAGTG**GAA**TTTGCAGG |
| V150FReverse | CCTGCAAA**TTC**CACTGA**GAA**TGT**ACT**AAA**CAG**GACTTGCTTAATC |
| S153EForward | GATTAAGCAAGTC**CTG**TTT**AGT**ACA**TTC**TCAGTG**GAA**TTTGCAGG |
| S153EReverse | CCTGCAAA**TTC**CACTGA**GAA**TGT**ACT**AAA**CAG**GACTTGCTTAATC |
| E228IForward | GCAAAGAAAC**ATC**AGA**CAT**GTGTTT**ACT**CAAAAGGTC |
| E228IReverse | GACCTTTTG**AGT**AAACAC**ATG**TCT**GAT**GTTTCTTTGC |
| N230HForward | GCAAAGAAAC**ATC**AGA**CAT**GTGTTT**ACT**CAAAAGGTC |
| N230HReverse | GACCTTTTG**AGT**AAACAC**ATG**TCT**GAT**GTTTCTTTGC |
| D233TForward | GCAAAGAAAC**ATC**AGA**CAT**GTGTTT**ACT**CAAAAGGTC |
| D233TReverse | GACCTTTTG**AGT**AAACAC**ATG**TCT**GAT**GTTTCTTTGC |
| R285VForward | GTGGTTTATTAC**GTA**ACGGGTTACACAACC |
| R285VReverse | GGTTGTGTAACCCGT**TAC**GTAATAAACCAC |
| Information of primers for construction of gshB mutant: mutation at L-lysine binding site | |
| D130QForward | CTAGGTATATTTAGATCA**CAG**TATTTGATTG |
| D130QReverse | CAATCAAATA**CTG**TGATCTAAATATACCTAG |
| E146LForward | GATTAAGCAAGTC**CTG**TTT**AGT**ACA**TTC**TCAGTG**GAA**TTTGCAGG |
| E146LReverse | CCTGCAAA**TTC**CACTGA**GAA**TGT**ACT**AAA**CAG**GACTTGCTTAATC |
| N148SForward | GATTAAGCAAGTC**CTG**TTT**AGT**ACA**TTC**TCAGTG**GAA**TTTGCAGG |
| N148SReverse | CCTGCAAA**TTC**CACTGA**GAA**TGT**ACT**AAA**CAG**GACTTGCTTAATC |
| G387NForward | CCACAGCGGGAA**AAT**GGCGGAAACAATGTTT |

TABLE 2-continued

| Primer name | Primer sequence |
|---|---|
| G387NReverse | AAACATTGTTTCCGCC**ATT**TTCCCGCTGTGG |
| I445DForward | CAGTGAACTAGGA**GAT**TATGGTTGCGTTC |
| I445DReverse | GAACGCAACCATA**ATC**TCCTAGTTCACTG |
| Primers for cloning Lal, gshB, PPK and ADK genes (the bold and underlined represent enzyme digestion sites) | |
| gshBForward | GCACTACTCCTATAA**CATATG**GCACACTATC |
| gshBReverse | GTTCTAGCATCATCT**CTCGAG**CATCTATGTG |
| PPKForward | GCAGAAA**CATATG**CCAATGGTTGCTGCAG |
| PPKReverse | GATGCCAGCAGCGAC**CTCGAG**ACCCCAGC |
| ADKForward | GAGGCAATCGC**CATATG**GTGGTATCGTTTATC |
| ADKReverse | CTGCCCGAAAGCAGATCTG**CTCGAG**CTTG |

Each enzyme can participate in catalysis reaction in the form of a crude enzyme solution containing the enzyme, a purified enzyme or an immobilized enzyme:

For example, the collected wet cells containing the enzyme were mixed in Tris-HCl buffer solution (25 mM, pH=8.0) (buffer solution A). After stirring evenly, the cells were crushed by high pressure and centrifuged at high speed to remove the cell wall. The collected supernatant was a crude enzyme solution, which was directly used for the subsequent catalysis reaction.

Alternatively, the above supernatant was gradually added with solid ammonium sulfate until the protein precipitated (35%-55%, w/v ammonium sulfate/buffer solution). The protein solid was then collected by high-speed centrifugation (10000 rpm, 12 min), slowly dissolved in Tris-HCl buffer solution (25 mM, pH=8.0), desalted by G25 desalting column (purchased from Sigma), separated and purified by DEAE Seplite FF (Xi'an Sunresin Co., Ltd.) anion exchange column to finally obtain a primarily purified enzyme. The SDS-PAGE gel image is shown in FIG. 2.

For the immobilization, reference can be made to the conventional methods for producing immobilized enzyme in the art.

According to the reaction route of the method of the present disclosure, the amount of each reaction material used can be adjusted according to actual situation.

Although the coding gene sequences of the enzymes can be known according to their amino acid sequences provided by the present disclosure, the specific coding gene sequences are still provided in the present disclosure as shown in Table 3:

TABLE 3

| Abbreviation | Sequence number | Gene sequence of enzyme |
|---|---|---|
| Lal | SEQ ID No. 9 | ATG ACG CAG GCC AAG GAA AAC ATC TTA GTT<br>GTG GTC GAT GGC TAC TCC TCA GGC AGT CAG<br>TTG CCT ACC CTG ATG GCG GAA TCC GGC TGG<br>AAG TGT GTT CAT GTC TCG TCC TCG GCT AAC<br>CCC CCG GAG TAT TAC CTG CGT ACA TAC CAT<br>AAG GAT GAG TAC ATA GCT CAC TTT GAG TAT<br>CAA GGT GAT ATA CAG TCA CTT GCT AGT GCT GTT<br>GAG GCG TGG CAT CCC GCC GCA GTT CTT CCT<br>GGT ACG GAA AGT GGA GTT ATT GTC GCT GAT<br>TTA CTG GCG GCT GCT TTG CAA TTG CCA GGC<br>AAT GAC CCG TCG ACC TCC CTG GCG AGA CGC<br>GAC AAA TAT ACG ATG CAT GAG TCA TTG AAA<br>GCG GTG GGA CTT CGG AGT ATG GAC CAT TTC<br>CTT GCC GTC GAT CGT GAT GCT TTA TCA GCT TGG<br>GCC GAG CGG GGA TCT TGG CCA GTG GTA ATT<br>AAA CCC CAG GCT TCG GCA GGC ACA GAC AGT<br>GTT ACA TTC TGC GCC GAT CAG GGA GAA TTA<br>TTA GAG TCG TTT GAT CAA TTG TTC GGC ACT GTG<br>AAC CAA TTG GGT GAA CGC AAT AAT GCA GTG<br>CTG GCT CAG CGT CTG TTG GTT GGT CCC GAG<br>TAC TTT ATC AAC GGA GTT TCT GGA CAT GGC AAA<br>CAC CTG ATT ACA GAG ATT TGG CGT GCA GAC<br>AAG CTG CCC GCA CCG GAC GGG GGT TGG ATA<br>TAC GAC CGG GCC GTG CTG TTT GAC CCG ACG<br>AGT CCC GAG ATG CAG GAG ATT GTC CGC TAC<br>GTG CAT GGA GTA TTA GAT GCC CTT GGC ATC CGC<br>TAT GGT GCG AAC CAT ACA GAG CTG ATC GTA<br>ACG GCT GAT GGC CCA ACA CTG ATA GAA TGT<br>GCC TCC CGT TTA TCC GGG GGA CTG CAT AGA |

TABLE 3-continued

| Abbreviation | Sequence number | Gene sequence of enzyme |
|---|---|---|
| | | CCT GCA GCG AAC TAT GCG GTT GGC GCA TCA CAA CTT GAC TTG GTC GGT AAA CTT GTA CGG GAA GGG GAA AGC GCT ATA GAT GAT ATA CTG CAA ACT TGG CAA CCT CAC CGC TAC GCA TTG TGG CAA GTC CAA TTC ATA TCG AAT CAA GAG GGA GTA GTG GCT CGG AGT TCG TAC GAC GAA CTT CTT AAA ACG TTG AAA TCC AAT GCC TGG TTG CAA CGG GCT CCG AAG GAA GGC GAT ACC GTA GTC AAG ACA GTC GAC CTG TTC AGC TCG CCC GGA ATA GTC TTT ATG TCA CAC GCA GAC GGT AAT GTT CTG CAC GAC GAT TAT CGG ACG GTC CGG GAA TGG GAG CGT ACC TCG CGC CTG TTC TCG GTG CAG TAA |
| GHS | SEQ ID No. 10 | ATG ACG CAG GCC AAG GAA AAC ATC TTA GTT GTG GTC GAT GGC TAC TCC TCA GGC AGT CAG TTG CCT ACC CTG ATG GCG GAA TCC GGC TGG AAG TGT GTT CAT GTC TCG TCC TCG GCT AAC CCC CCG GAG TAT TAC CTG CGT ACA TAC CAT AAG GAT GAG TAC ATA GCT CAC TTT GAG TAT CAA GGT GAT ATA CAG TCA CTT GCT AGT GCT GTT GAG GCG TGG CAT CCC GCC GCA GTT CTT CCT GGT ACG **AAA** AGT GGA GTT ATT GTC GCT GAT TTA CTG GCG GCT GCT TTG CAA TTG CCA GGC AAT GAC CCG TCG ACC TCC CTG GCG AGA CGC GAC AAA TAT ACG ATG CAT GAG TCA TTG AAA GCG GTG GGA CTT CGG AGT ATG GAC CAT TTC CTT GCC GTC GAT CGT GAT GCT TTA TCA GCT TGG GCC GAG CGG GGA TCT TGG CCA GTG GTA ATT AAA CCC CAG GCT TCG **CAC GAC** ACA GAC AGT GTT ACA TTC TGC GCC GAT CAG GGA GAA TTA TTA GAG TCG TTT GAT CAA TTG TTC GGC ACT GTG AAC CAA TTG GGT GAA CGC AAT AAT GCA GTG CTG GCT CAG CGT CTG TTG GTT GGT CCC GAG TAC TTT ATC AAC GGA GTT TCT GGA CAT GGC AAA CAC CTG ATT ACA GAG ATT TGG CGT GCA GAC AAG CTG CCC GCA CCG GAC GGG GGT TGG ATA TAC GAC CGG GCC GTG CTG TTT GAC CCG **ATC** AGT CCC GAG ATG CAG GAG ATT GTC CGC TAC GTG CAT GGA GTA TTA GAT GCC CTT GGC ATC CGC TAT GGT GCG AAC CAT ACA GAG CTG ATC GTA ACG GCT GAT GGC CCA ACA CTG ATA GAA TGT GCC TCC CGT TTA **CTC** GGG **TGG** CTG CAT AGA CCT GCA GCG AAC TAT GCG GTT GGC GCA TCA CAA CTT GAC TTG GTC GGT AAA CTT GTA CGG GAA GGG GAA AGC GCT ATA GAT GAT ATA CTG CAA ACT TGG CAA CCT CAC CGC TAC GCA TTG TGG CAA GTC CAA TTC ATA TCG AAT CAA GAG GGA GTA GTG GCT CGG AGT TCG TAC GAC GAA CTT CTT AAA ACG TTG AAA TCC AAT GCC TGG TTG CAA CGG GCT CCG AAG GAA GGC GAT ACC GTA GTC AAG ACA GTC GAC CTG TTC AGC TCG CCC GGA ATA GTC TTT ATG TCA CAC GCA GAC GGT AAT GTT CTG CAC GAC GAT TAT CGG ACG GTC CGG GAA TGG GAG CGT ACC TCG CGC CTG TTC TCG GTG CAG TAA |
| gshB | SEQ ID No. 11 | ATGGCACACTATCCACCTTCCAAGGATCAATTGAAT GAATTGATCCAGGAAGTTAACCAATGGGCTATCACT AATGGATTATCCATGTATCCTCCTAAATTCGAGGAG AACCCATCAAATGCATCGGTGTCACCAGTAACTATC TATCCAACCCCAATTCCTAGGAAATGTTTTGATGAG GCCGTTCAAATACAACCGGTATTCAATGAATTATAC GCCCGTATTACCCAAGATATGGCCCAACCTGATTCT TATTTACATAAAACAACTGAAGCGTTAGCTCTATCA GATTCCGAGTTTACTGGAAAACTGTGGTCTCTATAC CTTGCTACCTTAAAATCTGCACAGTACAAAAAGCA GAATTTTAGGCTAGGTATATTTAGATCAGATTATTTG ATTGATAAGAAAAAGGGTACTGAACAGATTAAGCA AGTCGAGTTTAATACAGTGTCAGTGTCATTTGCAGG CCTTAGCGAGAAAGTTGATAGATTGCACTCTTATTT AAATAGGGCAAACAAGTACGATCCTAAAGGACCAA TTTATAATGATCAAAATATGGTCATTTCTGATTCAGG ATACCTTTTGTCTAAGGCATTGGCCAAAGCTGTGGA ATCGTATAAGTCACAACAAAGTTCTTCTACAACTAG TGATCCTATTGTCGCATTCATTGTGCAAAGAAACGA GAGAAATGTGTTTGATCAAAAGGTCTTGGAATTGA |

TABLE 3-continued

| Abbreviation | Sequence number | Gene sequence of enzyme |
|---|---|---|
| | | ATCTGTTGGAAAAATTCGGTACCAAATCTGTTAGGT<br>TGACGTTTGATGATGTTAACGATAAATTGTTCATTGA<br>TGATAAAACGGGAAAGCTTTTCATTAGGGACACAG<br>AGCAGGAAATAGCGGTGGTTTATTACAGAACGGGT<br>TACACAACCACTGATTACACGTCCGAAAAGGACTG<br>GGAGGCAAGACTATTCCTCGAAAAAAGTTTCGCAA<br>TAAAGGCCCCAGATTTACTCACTCAATTATCTGGCT<br>CCAAGAAAATTCAGCAATTGTTGACAGATGAGGGC<br>GTATTAGGTAAATACATCTCCGATGCTGAGAAAAAG<br>AGTAGTTTGTTAAAAACTTTTGTCAAAATATATCCCT<br>TGGATGATACGAAGCTTGGCAGGGAAGGCAAGAG<br>GCTGGCATTAAGTGAGCCCTCTAAATACGTGTTAAA<br>ACCACAGCGGGAAGGTGGCGGAAACAATGTTTATA<br>AAGAAAATATTCCTAATTTTTTGAAAGGTATCGAAG<br>AACGTCACTGGGATGCATATATTCTCATGGAGTTGA<br>TTGAACCAGAGTTGAATGAAAATAATATTATATTACG<br>TGATAACAAATCTTACAACGAACCAATCATCAGTGA<br>ACTAGGAATTTATGGTTGCGTTCTATTTAACGACGA<br>GCAAGTTTTATCGAACGAATTTAGTGGCTCATTACT<br>AAGATCCAAATTTAATACTTCAAATGAAGGTGGAGT<br>GGCGGCAGGATTCGGATGTTTGGACAGTATTATTCT<br>TTACTAG |
| HKS | SEQ ID No. 12 | ATGGCACACTATCCACCTTCCAAGGATCAATTGAAT<br>GAATTGATCCAGGAAGTTAACCAATGGGCTATCACT<br>AATGGATTATCCATGTATCCTCCTAAATTCGAGGAG<br>AACCCATCAAATGCATCGGTGTCACCAGTAACTATC<br>TATCCAACCCCAATTCCTAGGAAATGTTTTGATGAG<br>GCCGTTCAAATACAACCGGTATTCAATGAATTATAC<br>GCCCGTATTACCCAAGATATGGCCCAACCTGATTCT<br>TATTTACATAAAACAACTGAAGCGTTAGCTCTATCA<br>GATTCCGAGTTTACTGGAAAACTGTGGTCTCTATAC<br>CTTGCTACCTTAAAATCTGCACAGTACAAAAAGCA<br>GAATTTTAGGCTAGGTATATTTAGATCA**CAG**TATTTG<br>ATTGATAAGAAAAAGGGTACTGAACAGATTAAGCA<br>AGTC**CTG**TTT**AGT**ACA**TTC**TCAGTG**GAA**TTTGCAG<br>GCCTTAGCGAGAAAGTTGATAGATTGCACTCTTATT<br>TAAATAGGGCAAACAAGTACGATCCTAAAGGACCA<br>ATTTATAATGATCAAAATATGGTCATTTCTGATTCAG<br>GATACCTTTTGTCTAAGGCATTGGCCAAAGCTGTGG<br>AATCGTATAAGTCACAACAAAGTTCTTCTACAACTA<br>GTGATCCTATTGTCGCATTCATTGTGCAAAGAAAC**A**<br>**TC**AGA**CAT**GTGTTT**ACT**CAAAAGGTCTTGGAATTG<br>AATCTGTTGGAAAAATTCGGTACCAAATCTGTTAGG<br>TTGACGTTTGATGATGTTAACGATAAATTGTTCATTG<br>ATGATAAAACGGGAAAGCTTTTCATTAGGGACACA<br>GAGCAGGAAATAGCGGTGGTTTATTAC**GTA**ACGGG<br>TTACACAACCACTGATTACACGTCCGAAAAGGACT<br>GGGAGGCAAGACTATTCCTCGAAAAAAGTTTCGCA<br>ATAAAGGCCCCAGATTTACTCACTCAATTATCTGGC<br>TCCAAGAAAATTCAGCAATTGTTGACAGATGAGGG<br>CGTATTAGGTAAATACATCTCCGATGCTGAGAAAAA<br>GAGTAGTTTGTTAAAAACTTTTGTCAAAATATATCC<br>CTTGGATGATACGAAGCTTGGCAGGGAAGGCAAGA<br>GGCTGGCATTAAGTGAGCCCTCTAAATACGTGTTAA<br>AACCACAGCGGGAA**AAT**GGCGGAAACAATGTTTAT<br>AAAGAAAATATTCCTAATTTTTTGAAAGGTATCGAA<br>GAACGTCACTGGGATGCATATATTCTCATGGAGTTG<br>ATTGAACCAGAGTTGAATGAAAATAATATTATATTAC<br>GTGATAACAAATCTTACAACGAACCAATCATCAGTG<br>AACTAGGA**GAT**TATGGTTGCGTTCTATTTAACGACG<br>AGCAAGTTTTATCGAACGAATTTAGTGGCTCATTAC<br>TAAGATCCAAATTTAATACTTCAAATGAAGGTGGAG<br>TGGCGGCAGGATTCGGATGTTTGGACAGTATTATTC<br>TTTACTAG |
| GHKS-1 | SEQ ID No. 13 | ATG ACG CAG GCC AAG GAA AAC ATC TTA GTT<br>GTG GTC GAT GGC TAC TCC TCA GGC AGT CAG<br>TTG CCT ACC CTG ATG GCG GAA TCC GGC TGG<br>AAG TGT GTT CAT GTC TCG TCC TCG GCT AAC<br>CCC CCG GAG TAT TAC CTG CGT ACA TAC CAT<br>AAG GAT GAG TAC ATA GCT CAC TTT GAG TAT<br>CAA GGT GAT ATA CAG TCA CTT GCT AGT GCT GTT<br>GAG GCG TGG CAT CCC GCC GCA GTT CTT CCT<br>GGT ACG **AAA** AGT GGA GTT ATT GTC GCT GAT<br>TTA CTG GCG GCT GCT TTG CAA TTG CCA GGC<br>AAT GAC CCG TCG ACC TCC CTG GCG AGA CGC |

TABLE 3-continued

| Abbreviation | Sequence number | Gene sequence of enzyme |
|---|---|---|
| | | GAC AAA TAT ACG ATG CAT GAG TCA TTG AAA |
| | | GCG GTG GGA CTT CGG AGT ATG GAC CAT TTC |
| | | CTT GCC GTC GAT CGT GAT GCT TTA TCA GCT TGG |
| | | GCC GAG CGG GGA TCT TGG CCA GTG GTA ATT |
| | | AAA CCC CAG GCT TCG **CAC GAC** ACA GAC AGT |
| | | GTT ACA TTC TGC GCC GAT CAG GGA GAA TTA |
| | | TTA GAG TCG TTT GAT CAA TTG TTC GGC ACT GTG |
| | | AAC CAA TTG GGT GAA CGC AAT AAT GCA GTG |
| | | CTG GCT CAG CGT CTG TTG GTT GGT CCC GAG |
| | | TAC TTT ATC AAC GGA GTT TCT GGA CAT GGC AAA |
| | | CAC CTG ATT ACA GAG ATT TGG CGT GCA GAC |
| | | AAG CTG CCC GCA CCG GAC GGG GGT TGG ATA |
| | | TAC GAC CGG GCC GTG CTG TTT GAC CCG **ATC** |
| | | AGT CCC GAG ATG CAG GAG ATT GTC CGC TAC |
| | | GTG CAT GGA GTA TTA GAT GCC CTT GGC ATC CGC |
| | | TAT GGT GCG AAC CAT ACA GAG CTG ATC GTA |
| | | ACG GCT GAT GGC CCA ACA CTG ATA GAA TGT |
| | | GCC TCC CGT TTA **CTC** GGG **TGG** CTG CAT AGA |
| | | CCT GCA GCG AAC TAT GCG GTT GGC GCA TCA |
| | | CAA CTT GAC TTG GTC GGT AAA CTT GTA CGG |
| | | GAA GGG GAA AGC GCT ATA GAT GAT ATA CTG |
| | | CAA ACT TGG CAA CCT CAC CGC TAC GCA TTG |
| | | TGG CAA GTC CAA TTC ATA TCG AAT CAA GAG |
| | | GGA GTA GTG GCT CGG AGT TCG TAC GAC GAA |
| | | CTT CTT AAA ACG TTG AAA TCC AAT GCC TGG TTG |
| | | CAA CGG GCT CCG AAG GAA GGC GAT ACC GTA |
| | | GTC AAG ACA GTC GAC CTG TTC AGC TCG CCC |
| | | GGA ATA GTC TTT ATG TCA CAC GCA GAC GGT AAT |
| | | GTT CTG CAC GAC GAT TAT CGG ACG GTC CGG |
| | | GAA TGG GAG CGT ACC TCG CGC CTG TTC TCG |
| | | GTG CAG **GGT GGT GGT GGA TCA GGG GGT** |
| | | **GGG GGT TCA GGC GGT GGC GGA TCC GGC** |
| | | **GGG GGT GGT TCC** ATG GCA CAC TAT CCA CCT |
| | | TCC AAG GAT CAA |
| | | TTGAATGAATTGATCCAGGAAGTTAACCAATGGGCT |
| | | ATCACTAATGGATTATCCATGTATCCTCCTAAATTCG |
| | | AGGAGAACCCATCAAATGCATCGGTGTCACCAGTA |
| | | ACTATCTATCCAACCCCAATTCCTAGGAAATGTTTTG |
| | | ATGAGGCCGTTCAAATACAACCGGTATTCAATGAAT |
| | | TATACGCCCGTATTACCCAAGATATGGCCCAACCTG |
| | | ATTCTTATTTACATAAAACAACTGAAGCGTTAGCTCT |
| | | ATCAGATTCCGAGTTTACTGGAAAACTGTGGTCTCT |
| | | ATACCTTGCTACCTTAAAATCTGCACAGTACAAAAA |
| | | GCAGAATTTTAGGCTAGGTATATTTAGATCA**CAG**TAT |
| | | TTGATTGATAAGAAAAAGGGTACTGAACAGATTAA |
| | | GCAAGTC**CTG**TTT**AGT**ACA**TTC**TCAGTG**GAA**TTTG |
| | | CAGGCCTTAGCGAGAAAGTTGATAGATTGCACTCTT |
| | | ATTTAAATAGGGCAAACAAGTACGATCCTAAAGGA |
| | | CCAATTTATAATGATCAAAATATGGTCATTTCTGATT |
| | | CAGGATACCTTTTGTCTAAGGCATTGGCCAAAGCTG |
| | | TGGAATCGTATAAGTCACAACAAAGTTCTTCTACAA |
| | | CTAGTGATCCTATTGTCGCATTCATTGTGCAAAGAA |
| | | AC**ATC**AGA**CAT**GTGTTT**ACT**CAAAAGGTCTTGGAA |
| | | TTGAATCTGTTGGAAAAATTCGGTACCAAATCTGTT |
| | | AGGTTGACGTTTGATGATGTTAACGATAAATTGTTC |
| | | ATTGATGATAAAACGGGAAAGCTTTTCATTAGGGAC |
| | | ACAGAGCAGGAAATAGCGGTGGTTTATTAC**GTA**AC |
| | | GGGTTACACAACCACTGATTACACGTCCGAAAAGG |
| | | ACTGGGAGGCAAGACTATTCCTCGAAAAAAGTTTC |
| | | GCAATAAAGGCCCCAGATTTACTCACTCAATTATCT |
| | | GGCTCCAAGAAAATTCAGCAATTGTTGACAGATGA |
| | | GGGCGTATTAGGTAAATACATCTCCGATGCTGAGAA |
| | | AAAGAGTAGTTTGTTAAAAACTTTTGTCAAAATATA |
| | | TCCCTTGGATGATACGAAGCTTGGCAGGGAAGGCA |
| | | AGAGGCTGGCATTAAGTGAGCCCTCTAAATACGTGT |
| | | TAAAACCACAGCGGGAA**AAT**GGCGGAAACAATGT |
| | | TTATAAAGAAAATATTCCTAATTTTTTGAAAGGTATC |
| | | GAAGAACGTCACTGGGATGCATATATTCTCATGGAG |
| | | TTGATTGAACCAGAGTTGAATGAAAATAATATTATAT |
| | | TACGTGATAACAAATCTTACAACGAACCAATCATCA |
| | | GTGAACTAGGA**GAT**TATGGTTGCGTTCTATTTAACG |
| | | ACGAGCAAGTTTTATCGAACGAATTTAGTGGCTCAT |
| | | TACTAAGATCCAAATTTAATACTTCAAATGAAGGTG |
| | | GAGTGGCGGCAGGATTCGGATGTTTGGACAGTATTA |
| | | TTCTTTACTAG |

TABLE 3-continued

| Abbreviation | Sequence number | Gene sequence of enzyme |
|---|---|---|
| GHKS-2 | SEQ ID No. 14 | ATG ACG CAG GCC AAG GAA AAC ATC TTA GTT<br>GTG GTC GAT GGC TAC TCC TCA GGC AGT CAG<br>TTG CCT ACC CTG ATG GCG GAA TCC GGC TGG<br>AAG TGT GTT CAT GTC TCG TCC TCG GCT AAC<br>CCC CCG GAG TAT TAC CTG CGT ACA TAC CAT<br>AAG GAT GAG TAC ATA GCT CAC TTT GAG TAT<br>CAA GGT GAT ATA CAG TCA CTT GCT AGT GCT GTT<br>GAG GCG TGG CAT CCC GCC GCA GTT CTT CCT<br>GGT ACG **AAA** AGT GGA GTT ATT GTC GCT GAT<br>TTA CTG GCG GCT GCT TTG CAA TTG CCA GGC<br>AAT GAC CCG TCG ACC TCC CTG GCG AGA CGC<br>GAC AAA TAT ACG ATG CAT GAG TCA TTG AAA<br>GCG GTG GGA CTT CGG AGT ATG GAC CAT TTC<br>CTT GCC GTC GAT CGT GAT GCT TTA TCA GCT TGG<br>GCC GAG CGG GGA TCT TGG CCA GTG GTA ATT<br>AAA CCC CAG GCT TCG **CAC GAC** ACA GAC AGT<br>GTT ACA TTC TGC GCC GAT CAG GGA GAA TTA<br>TTA GAG TCG TTT GAT CAA TTG TTC GGC ACT GTG<br>AAC CAA TTG GGT GAA CGC AAT AAT GCA GTG<br>CTG GCT CAG CGT CTG TTG GTT GGT CCC GAG<br>TAC TTT ATC AAC GGA GTT TCT GGA CAT GGC AAA<br>CAC CTG ATT ACA GAG ATT TGG CGT GCA GAC<br>AAG CTG CCC GCA CCG GAC GGG GGT TGG ATA<br>TAC GAC CGG GCC GTG CTG TTT GAC CCG **ATC**<br>AGT CCC GAG ATG CAG GAG ATT GTC CGC TAC<br>GTG CAT GGA GTA TTA GAT GCC CTT GGC ATC CGC<br>TAT GGT GCG AAC CAT ACA GAG CTG ATC GTA<br>ACG GCT GAT GGC CCA ACA CTG ATA GAA TGT<br>GCC TCC CGT TTA **CTC** GGG **TGG** CTG CAT AGA<br>CCT GCA GCG AAC TAT GCG GTT GGC GCA TCA<br>CAA CTT GAC TTG GTC GGT AAA CTT GTA CGG<br>GAA GGG GAA AGC GCT ATA GAT GAT ATA CTG<br>CAA ACT TGG CAA CCT CAC CGC TAC GCA TTG<br>TGG CAA GTC CAA TTC ATA TCG AAT CAA GAG<br>GGA GTA GTG GCT CGG AGT TCG TAC GAC GAA<br>CTT CTT AAA ACG TTG AAA TCC AAT GCC TGG TTG<br>CAA CGG GCT CCG AAG GAA GGC GAT ACC GTA<br>GTC AAG ACA GTC GAC CTG TTC AGC TCG CCC<br>GGA ATA GTC TTT ATG TCA CAC GCA GAC GGT AAT<br>GTT CTG CAC GAC GAT TAT CGG ACG GTC CGG<br>GAA TGG GAG CGT ACC TCG CGC CTG TTC TCG<br>GTG CAG **GGT GGT GGG GGA TCT GAG GCT GCG**<br>**GCT AAA GAG GCG GCA GCA AAA GGA GGA GGC**<br>**GGA AGC** ATG GCA CAC TAT CCA CCT TCC AAG<br>GAT CAA<br>TTGAATGAATTGATCCAGGAAGTTAACCAATGGGCT<br>ATCACTAATGGATTATCCATGTATCCTCCTAAATTCG<br>AGGAGAACCCATCAAATGCATCGGTGTCACCAGTA<br>ACTATCTATCCAACCCCAATTCCTAGGAAATGTTTTG<br>ATGAGGCCGTTCAAATACAACCGGTATTCAATGAAT<br>TATACGCCCGTATTACCCAAGATATGGCCCAACCTG<br>ATTCTTATTTACATAAAACAACTGAAGCGTTAGCTCT<br>ATCAGATTCCGAGTTTACTGGAAAACTGTGGTCTCT<br>ATACCTTGCTACCTTAAAATCTGCACAGTACAAAAA<br>GCAGAATTTTAGGCTAGGTATATTTAGATCA**CAG**TAT<br>TTGATTGATAAGAAAAAGGGTACTGAACAGATTAA<br>GCAAGTC**CTG**TTT**AGT**ACA**TTC**TCAGTG**GAA**TTTG<br>CAGGCCTTAGCGAGAAAGTTGATAGATTGCACTCTT<br>ATTTAAATAGGGCAAACAAGTACGATCCTAAAGGA<br>CCAATTTATAATGATCAAAATATGGTCATTTCTGATT<br>CAGGATACCTTTTGTCTAAGGCATTGGCCAAAGCTG<br>TGGAATCGTATAAGTCACAACAAAGTTCTTCTACAA<br>CTAGTGATCCTATTGTCGCATTCATTGTGCAAAGAA<br>AC**ATC**AGA**CAT**GTGTTT**ACT**CAAAAGGTCTTGGAA<br>TTGAATCTGTTGGAAAAATTCGGTACCAAATCTGTT<br>AGGTTGACGTTTGATGATGTTAACGATAAATTGTTC<br>ATTGATGATAAAACGGGAAAGCTTTTCATTAGGGAC<br>ACAGAGCAGGAAATAGCGGTGGTTTATTAC**GTA**AC<br>GGGTTACACAACCACTGATTACACGTCCGAAAAGG<br>ACTGGGAGGCAAGACTATTCCTCGAAAAAAGTTTC<br>GCAATAAAGGCCCCAGATTTACTCACTCAATTATCT<br>GGCTCCAAGAAAATTCAGCAATTGTTGACAGATGA<br>GGGCGTATTAGGTAAATACATCTCCGATGCTGAGAA<br>AAAGAGTAGTTTGTTAAAAACTTTTGTCAAAATATA<br>TCCCTTGGATGATACGAAGCTTGGCAGGGAAGGCA<br>AGAGGCTGGCATTAAGTGAGCCCTCTAAATACGTGT<br>TAAAACCACAGCGGGAA**AAT**GGCGGAAACAATGT |

TABLE 3-continued

| Abbreviation | Sequence number | Gene sequence of enzyme |
|---|---|---|
| | | TTATAAAGAAAATATTCCTAATTTTTTGAAAGGTATC<br>GAAGAACGTCACTGGGATGCATATATTCTCATGGAG<br>TTGATTGAACCAGAGTTGAATGAAAATAATATTATAT<br>TACGTGATAACAAATCTTACAACGAACCAATCATCA<br>GTGAACTAGGA**GAT**TATGGTTGCGTTCTATTTAACG<br>ACGAGCAAGTTTTATCGAACGAATTTAGTGGCTCAT<br>TACTAAGATCCAAATTTAATACTTCAAATGAAGGTG<br>GAGTGGCGGCAGGATTCGGATGTTTGGACAGTATTA<br>TTCTTTACTAG |
| PPK | SEQ ID No. 15 | ATGCCAATGGTTGCTGCAGTTGAGTTCGCCAAAAG<br>TCCGGCCGAAGTACTGAGGGTTGGATCGGGGTTTT<br>CGCTGGCAGGCGTGGATCCCGAATCCACACCCGGC<br>TACACCGGTGTGAAAGCTGATGGCAAGGCGTTGCT<br>TGCCGCGCAGGACGCGCGGCTGGCGGAACTGCAG<br>GAAAAGCTCTTCGCCGAAGGAAAGTTCGGCAACC<br>CCAAACGGCTCCTGCTCATCCTTCAGGCCATGGATA<br>CTGCGGGCAAGGGCGGCATTGTCAGCCACGTTGTT<br>GGCGCCATGGACCCGCAAGGCGTACAACTGACCGC<br>CTTCAAAGCGCCTACGGACGAGGAAAAGTCGCAC<br>GACTTCCTCTGGAGAATCGAAAAACAAGTCCCTGC<br>CGCCGGAATGGTGGGGGTGTTCGACCGCTCGCAGT<br>ACGAAGACGTGCTGATCCACCGTGTCCATGGCTGG<br>GCGGACGCTGCCGAACTGGAGCGCCGGTACGCCGC<br>GATCAACGACTTTGAGTCACGCCTGACCGAGCAGG<br>GAACCACCATCGTCAAGGTCATGCTCAATATCAGCA<br>AGGACGAACAGAAAAAGCGTTTGATCGCCCGGTTG<br>GACGATCCCAGCAAGCACTGGAAATACAGTCGCGG<br>CGACCTCGCGGAACGTGCGTACTGGGATGACTACA<br>TGGACGCCTACAGCGTTGCCTTCGAGAAGACCTCC<br>ACAGAGATTGCTCCTTGGCACGTGGTGCCGGCAAA<br>CAAGAAGTGGTACGCACGCATCGCAGTCCAGCAAC<br>TGCTGCTGGATGCCCTCGGCGGTTTGCAGCTGGAC<br>TGGCCCAAAGCTGACTTCGATGTCGCCGCTGAGCG<br>CGCCCTCGTGGTGGAATCCTAG |
| ADK | SEQ ID No. 16 | ATGCGTATCATTCTGCTTGGCGCTCCGGGCGCGGGG<br>AAAGGGACTCAGGCTCAGTTCATCATGGAGAAATA<br>TGGTATTCCGCAAATCTCCACTGGCGATATGCTGCG<br>TGCTGCGGTCAAATCTGGCTCCGAGCTGGGTAAAC<br>AAGCAAAAGACATTATGGATGCTGGCAAACTGGTC<br>ACCGACGAACTGGTGATCGCGCTGGTTAAAGAGCG<br>CATTGCTCAGGAAGACTGCCGTAATGGTTTCCTGTT<br>GGACGGCTTCCCGCGTACCATTCCGCAGGCAGACG<br>CGATGAAAGAAGCGGGCATCAATGTTGATTACGTTC<br>TGGAATTCGACGTACCGGACGAACTGATCGTTGAC<br>CGTATCGTCGGTCGCCGCGTTCATGCGCCGTCTGGT<br>CGTGTTTATCACGTTAAATTCAATCCGCCGAAAGTA<br>GAAGGCAAAGACGACGTTACCGGTGAAGAACTGA<br>CTACCCGTAAAGATGATCAGGAAGAGACCGTACGT<br>AAACGTCTGGTTGAATACCATCAGATGACAGCACC<br>GCTGATCGGCTACTACTCCAAAGAAGCAGAAGCGG<br>GTAATACCAAATACGCGAAAGTTGACGGCACCAAG<br>CCGGTTGCTGAAGTTCGCGCTGATCTGGAAAAAAT<br>CCTCGGCTAA |

The present disclosure is further illustrated below in conjunction with examples.

Example 1: Preparation of Prezatide by Catalysis (Combination of GHS, HKS, PPK and ADK)

The gene fragments of ADK, gshB and PPK were amplified with chromosomes of *Escherichia coli* K12, *Saccharomyces cerevisiae* (ATCC 204508) and *Paenarthrobacter aurescens* TC1 purchased from ATCC as templates by PCR using the above corresponding primers, subjected to enzyme digestion using the Nde I/Xho I purchased from NEB Company, and connected to a pET28a plasmid (purchased from Addgene) digested with the same enzyme. Then the plasmid was transformed into *E. coli* DH5a cells (purchased from Tsingke Biotechnology), and verified by colony PCR and gene sequencing. Lal gene fragment was synthesized by Anhui General Biology Co., Ltd., and subcloned into a pET28a plasmid. Then multi-site mutant enzyme genes GHS and HKS were constructed with Lal and gshB genes as templates using the mutation primers in Table 2 (by conventional PCR amplification). The above GHS, HKS, PPK and ADK plasmids constructed with the pET-28a vector were transferred into *E. coli* BL21 (DE3) (purchased from Anhui General Biology Co., Ltd.) strains, which were then cultured in a small-scale in 5 ml of LB culture medium containing 50 μM Kanamycin at 37° C. When the cells grew to an OD value of 0.5-0.8, 0.5 mM isopropyl-β-D-thiogalactopyranoside (IPTG) was added to induce protein expression at 37° C. for 3 h. Finally the cells were collected, disrupted by freeze-thaw method, and centrifuged at high speed, and the collected supernatant was subjected to sodium dodecyl sulfate polyacrylamide gel electrophoresis (SDS-PAGE) to confirm the protein expression. The strains with correct protein expression were cultured step by step in a 5 liter fermenter to be induced for expression under the condition of 1.0 mM IPTG at 37° C. for 4 h, and wet cells were collected to be 35-55 g. Then after the cells and an appropriate amount of Tris·HCl buffer solution (25 mM, pH=8.0) were mixed evenly, the cells were crushed with a high-pressure crusher at low temperature and centrifuged at high speed to remove the cell wall to obtain an enzyme solution, which was stored in a refrigerator at 4° C. for later use. The LB culture medium was composed of 1% tryptone, 0.5% yeast powder, 1% NaCl, 1% dipotassium phosphate, 1% dipotassium phosphate and 5% glycerol.

Figure 3:
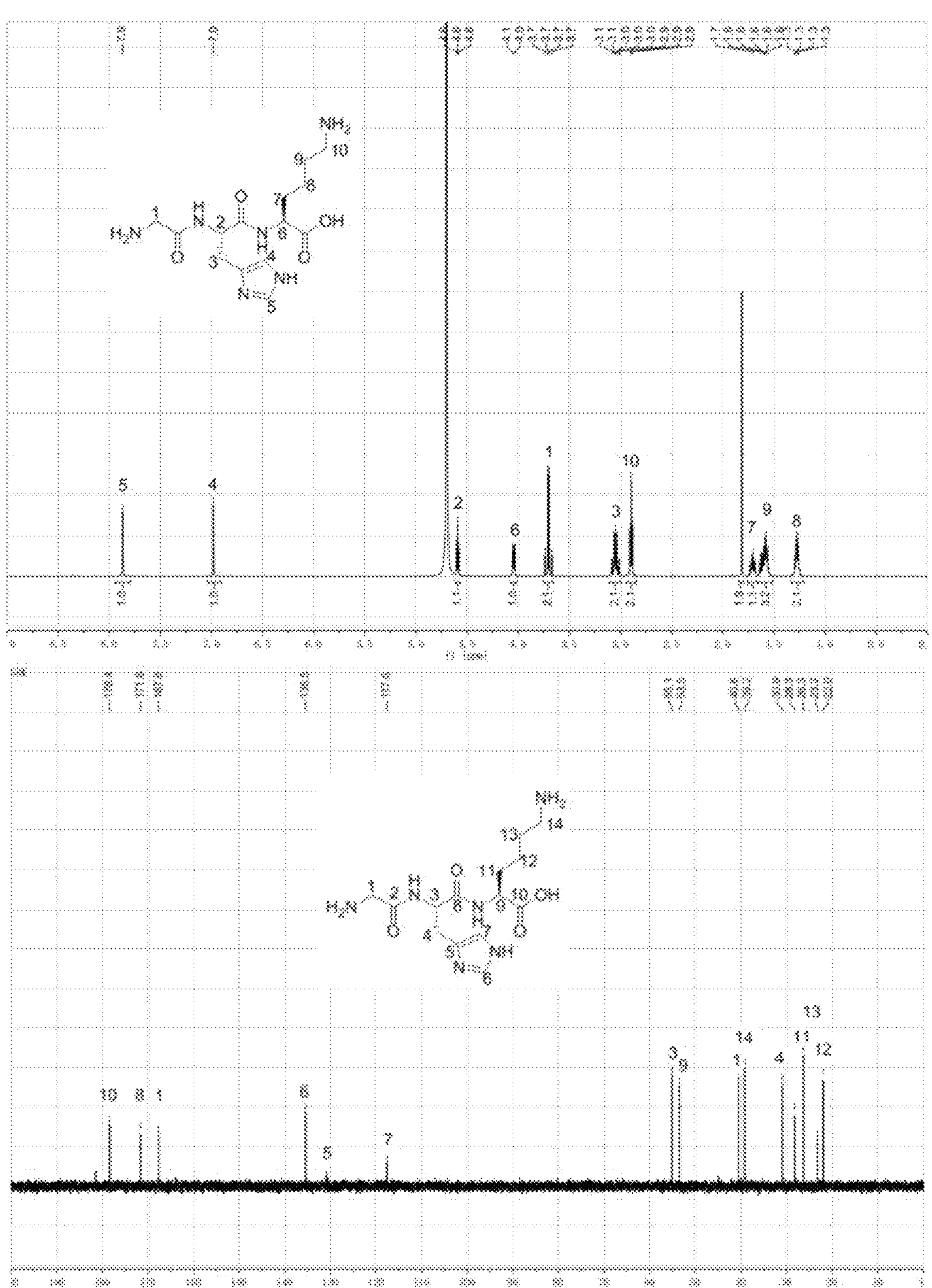
FIG. 3 shows the nuclear magnetic spectrum of the purified prezatide with 600 M Varian in $D_2O$ solution; where the upper panel shows $^{1}$H-NMR, and the lower panel shows $^{13}$C-NMR.

1 L of 100 mM tris(hydroxymethyl)aminomethane hydrochloride (Tris·HCl) solution at pH 8.0 was added with 15 g of glycine (200 mM), 31 g of L-histidine (200 mM), 29.2 g of L-lysine (200 mM), 5.6 g of adenosine disodium triphosphate (10 mM) providing ATP, 1.8 g of magnesium chloride (20 mM), 3.75 g of potassium chloride (20 mM) and 51.6 g of polyphosphoric acid (Sigma, 25 poly, 500 mM monophosphoric acid). After adjusting pH to 8.0, 1000 U of GHS enzyme solution, 1500 U of HKS enzyme solution, 2000 U of PPK and 1200 U of ADK enzyme solution were added. The reaction system was stirred slowly at room temperature for 6 h. During the reaction, the system was maintained at pH of 6.5-9.0 by adding aqueous solutions of HCl and NaOH. Then it was detected that most of the raw materials were consumed by detecting the residual raw material histidine in the reaction solution using L-histidine detection kit of ProFoldin. Finally, the pH of the reaction solution was adjusted to terminate the reaction and precipitate the protein in the reaction solution by adding acid to adjust the solution to pH of 1.5 and stirring rapidly. The protein precipitate was removed by filtration, and then the solution was adjusted back to pH 7.0. The salt was removed by reverse osmosis. The impurities containing phosphoric acid were removed by D201 anion exchange resin, where the deionized water was used as eluent, prezatide GHK was directly eluted out due to its weak binding ability to resin. After lyophilization, the crude product of glycine-L-histidine-L-lysine was crystallized with pure water and ethanol of 1:(1-3) v/v to obtain 59 g of grey-white solid with a yield of 87% and a purity of 96.0%. The nuclear magnetic spectrum of the purified prezatide with 600 M Varian in $D_2O$ solution is shown in FIG. 3, where the upper panel shows $^1$H-NMR, and the lower panel shows $^{13}$C-NMR.

Example 2: Preparation of Prezatide by Catalysis (Combination of GHKS-1, PPK and ADK)

The gene fragment GHKS-1 of prezatide GHK synthetase was synthesized by Anhui General Biology Co., Ltd., and subcloned into a pET28a plasmid. Similar to Example 1, the plasmid was transformed into *E. coli* BL21 (DE3) strain for protein expression in a small amount, and then amplified in a 5 L fermenter for fermentation, and wet cells were collected to be about 40 g. The enzyme solutions of polyphosphate kinase PPK and adenylate kinase ADK prepared in Example 1 were directly used for the subsequent preparation reactions.

Under the similar reaction conditions to those in Example 1, 1 L of 100 mM tris(hydroxymethyl)aminomethane hydrochloride solution at pH 8.0 was added with 11.2 g of glycine (150 mM), 23.2 g of L-histidine (150 mM), 21.9 g of L-Lysine (150 mM), 5.6 g of adenosine disodium triphosphate (10 mM) providing ATP, 1.8 g of magnesium chloride (20 mM), 3.75 g of potassium chloride (20 mM) and 20.6 g of polyphosphoric acid (200 mM monophosphoric acid). After adjusting pH to 8.0, 2000 U of GHKS-1 enzyme solution, 1500 U of PPK and 1000 U of ADK enzyme solution were added. The reaction was performed for 10 h at room temperature, and it was detected that L-histidine in the reaction solution was completely consumed. Finally, HCl solution was added to the reaction to adjust pH to 1.5 to terminate the reaction and precipitate the protein. The protein precipitate was removed by filtration. Then the supernatant was adjusted back to pH 7.0, and the salt was removed by reverse osmosis. Finally the impurities containing phosphoric acid in the solution were removed by an anion exchange column. The eluent was concentrated and purified by crystallization with ethanol and water to obtain 31.6 g of pure prezatide with a yield of 62% and a purity of 91.2%. The nuclear magnetic spectrum of the purified prezatide with 600 M Varian in $D_2O$ solution is the same as in Example 1.

Example 3: Preparation of Prezatide by Catalysis (Combination of GHKS-1, PPK and ADK)

Similar to Example 2, the gene fragment GHKS-2 of prezatide GHK synthetase was synthesized by Anhui General Biology Co., Ltd., and subcloned into a pET28a plasmid. After the protein was verified through expression in a small amount, the preparation was directly amplified, and the overexpressed cell lysate was stored at 4° C. for later use. The enzyme solutions of polyphosphate kinase PPK and adenylate kinase ADK prepared in Example 1 can be directly used in this enzymatic reaction.

Similar to Example 2, 1 L of 100 mM tris(hydroxymethyl) aminomethane hydrochloride solution at pH 8.0 was added with 15 g of glycine (200 mM), 31 g of L-histidine (200 mM), 29.2 g of L-Lysine (200 mM), 5.6 g of adenosine disodium triphosphate ATP (10 mM), 1.8 g of magnesium chloride (20 mM), 3.75 g of potassium chloride (20 mM) and 51.6 g of polyphosphoric acid (500 mM monophosphoric acid). After adjusting pH to 8.0, 2000 U of GHKS-2 enzyme solution, 2000 U of PPK and 1500 U of ADK enzyme solution were added. The reaction system was stirred at room temperature for 7 h while maintaining the pH value of the reaction system at 6.5-9.0. Then it was detected that most of the raw material histidine was converted completely. HCl aqueous solution was added to terminate the reaction and precipitate the protein by denaturation. Similar to the above, the salt was finally removed, and the impurities containing phosphoric acid in the reaction was removed with an anion exchange column. The crude solution of prezatide was concentrated and crystallized to finally obtain 61.8 g of grey-white solid with a yield of 91% and a purity of 94.5%. The nuclear magnetic spectrum of the purified prezatide with 600 M Varian in $D_2O$ solution is the same as in Example 1.

The above are only preferred embodiments of the present disclosure, and it should be noted that for those of ordinary skill in the art, several improvements and modifications can also be made without departing from the principle of the present disclosure, and these improvements and modifications should also be considered as the protection scope of the present disclosure.

The invention claimed is:

1. A mutant enzyme, wherein it comprises glycine and L-histidine ligase GHS and tripeptide ligase HKS, or is a fusion enzyme of the two;

wherein, the glycine and L-histidine ligase GHS is an enzyme with only mutations T244I, S290L, G292W, E84K, A158H, and G159D as compared to SEQ ID NO: 1, and the tripeptide ligase HKS is an enzyme with only mutations V150F, S153E, E228I, N230H, D233T, R285V, D130Q, E146L, N148S, G387N, and 1445D as compared to SEQ ID NO: 3.

2. A method for producing prezatide by enzymatic catalysis method, comprising subjecting reaction raw materials of glycine, L-histidine, L-lysine and ATP or salt thereof to enzymatic catalysis reaction with the mutant enzyme according to claim 1 in a reaction medium within a pH range of the mutant enzyme according to claim 1 to produce prezatide.

3. The method according to claim 2, wherein the pH range of the mutant enzyme is 6.5-9.0.

4. The method according to claim 2, wherein the reaction medium is a buffer solution.

5. The method according to claim 2, further comprising adding reaction raw materials of PPK and ADK or a fusion protein of the two, polyphosphoric acid, magnesium chloride and potassium chloride.

6. The method according to claim 2, further comprising a purification step selected from the group consisting of removing protein impurities, removing residual reaction raw materials, desalting, removing phosphoric acid, crystallization and a combination thereof.

7. An enzyme preparation comprising the mutant enzyme according to claim 1, wherein the enzyme preparation is a host cell expressing the mutant enzyme, an enzyme solution of the mutant enzyme or an immobilized enzyme of the mutant enzyme.

* * * * *